(12) United States Patent
Connor

(10) Patent No.: US 11,747,769 B2
(45) Date of Patent: Sep. 5, 2023

(54) SMART WATCH WITH VARIABLE-CONFIGURATION DISPLAY

(71) Applicant: Robert A. Connor, St. Paul, MN (US)

(72) Inventor: Robert A. Connor, St. Paul, MN (US)

(73) Assignee: Medibotics LLC, St. Paul, MN (US)

( * ) Notice: Subject to any disclaimer, the term of this patent is extended or adjusted under 35 U.S.C. 154(b) by 0 days.

(21) Appl. No.: 17/871,952

(22) Filed: Jul. 24, 2022

(65) Prior Publication Data

US 2022/0357707 A1    Nov. 10, 2022

Related U.S. Application Data

(63) Continuation-in-part of application No. 17/515,509, filed on Oct. 31, 2021, and a continuation-in-part of application No. 16/926,748, filed on Jul. 12, 2020, now abandoned, and a continuation-in-part of application No. 16/819,147, filed on Mar. 15, 2020, now Pat. No. 11,429,151, said application No. 17/515,509 is a continuation-in-part of application No. 16/926,748, filed on Jul. 12, 2020, now abandoned, which is a continuation-in-part of application No. 15/431,769, filed on Feb. 14, 2017, now abandoned, said application No. 16/819,147 is a continuation-in-part of application No. 16/598,514, filed on Oct. 10, 2019, now abandoned, and a continuation-in-part of application No. 15/294,746, filed on Oct. 16, 2016, now Pat. No. 10,627,861, said application No. 16/598,514 is a continuation-in-part of application No. 15/294,746, filed on Oct. 16, 2016, now Pat. No. 10,627,861, and a continuation-in-part (Continued)

(51) Int. Cl.
*G04G 9/00* (2006.01)
*G06F 1/16* (2006.01)
*A61B 5/00* (2006.01)

(52) U.S. Cl.
CPC ............. *G04G 9/007* (2013.01); *G06F 1/163* (2013.01); *G06F 1/1647* (2013.01); *A61B 5/681* (2013.01)

(58) Field of Classification Search
CPC ...... G04G 17/083; G04G 21/02; G04G 9/007; G04G 17/08; G04G 21/00; G06F 1/3265; G06F 1/163; G06F 1/1641; G06F 1/1624; G06F 1/1647; A61B 5/7445; A61B 5/681; H04N 23/51
See application file for complete search history.

(56) References Cited

U.S. PATENT DOCUMENTS 7,558,057 B1    7/2009    Naksen et al.
8,279,716 B1    10/2012    Gossweiler et al.
(Continued)

FOREIGN PATENT DOCUMENTS

CN    203858462 U    12/2013
WO    WO/2019/084971    9/2019

*Primary Examiner* — Yaron Cohen

(57) ABSTRACT

This invention is a smart watch with variable-configuration displays which combine to provide a larger combined display when needed. When a person does not need a large display area, then a plurality of displays on the watch fit around the person's wrist and/or arm in a relatively compact first configuration. When the person needs a larger display area, then the plurality of displays are moved into a second configuration which creates a large, coplanar, combined display.

1 Claim, 17 Drawing Sheets

Related U.S. Application Data of application No. 14/623,337, filed on Feb. 16, 2015, now Pat. No. 9,582,035, said application No. 15/431,769 is a continuation-in-part of application No. 14/623,337, filed on Feb. 16, 2015, now Pat. No. 9,582,035, said application No. 15/294,746 is a continuation-in-part of application No. 14/623,337, filed on Feb. 16, 2015, now Pat. No. 9,582,035.

(60) Provisional application No. 62/876,213, filed on Jul. 19, 2019, provisional application No. 62/882,560, filed on Aug. 4, 2019, provisional application No. 62/820,337, filed on Mar. 19, 2019, provisional application No. 62/115,691, filed on Feb. 13, 2015, provisional application No. 62/113,423, filed on Feb. 7, 2015, provisional application No. 62/111,163, filed on Feb. 3, 2015, provisional application No. 62/106,856, filed on Jan. 23, 2015, provisional application No. 62/100,217, filed on Jan. 6, 2015, provisional application No. 61/948,124, filed on Mar. 5, 2014, provisional application No. 61/944,090, filed on Feb. 25, 2014.

(56) References Cited

U.S. PATENT DOCUMENTS

| | | |
|---|---|---|
| 8,379,488 B1 | 2/2013 | Gossweiler et al. |
| 8,851,372 B2 | 10/2014 | Zhou et al. |
| 8,902,714 B2 | 12/2014 | Gossweiler et al. |
| 9,933,756 B2 | 4/2018 | Tang |
| 10,152,028 B2 | 12/2018 | Kim |
| 10,319,331 B2 | 6/2019 | Pasupathi |
| 10,755,668 B2 | 8/2020 | Pasupathi |
| 2009/0219788 A1 | 9/2009 | Henley |
| 2013/0275910 A1 | 10/2013 | Kim et al. |
| 2015/0029227 A1* | 1/2015 | Park ............ G06F 1/163 345/659 |
| 2015/0378393 A1 | 12/2015 | Erad et al. |
| 2016/0239190 A1 | 8/2016 | Forutanpour et al. |
| 2016/0240154 A1 | 8/2016 | Forutanpour et al. |
| 2016/0267310 A1 | 9/2016 | Al Nasser et al. |
| 2018/0018930 A1 | 1/2018 | Pasupathi |
| 2018/0120901 A1 | 5/2018 | Jin et al. |
| 2020/0042037 A1 | 2/2020 | Sun |

\* cited by examiner

Device in
first configuration --
bottom and middle displays
recessed in housing under
top display; and band
configured at first
(narrow) width Device in
second configuration --
bottom and middle displays
extended (slid/telescoped)
out from under top display;
and band extended
proximally to second
(wide) width

SMART WATCH WITH VARIABLE-CONFIGURATION DISPLAY

CROSS-REFERENCE TO RELATED APPLICATIONS

This application is a continuation in part of U.S. patent application Ser. No. 17/515,509 filed on 2021 Oct. 31. This application is a continuation in part of U.S. patent application Ser. No. 16/926,748 filed on 2020 Jul. 12. This application is a continuation in part of U.S. patent application Ser. No. 16/819,147 filed on 2020 Mar. 15.

U.S. patent application Ser. No. 17/515,509 was a continuation in part of U.S. patent application Ser. No. 16/926,748 filed on 2020 Jul. 12. U.S. patent application Ser. No. 16/926,748 was a continuation in part of U.S. patent application Ser. No. 15/431,769 filed on 2017 Feb. 14. U.S. patent application Ser. No. 16/926,748 claimed the priority benefit of U.S. provisional patent application 62/876,213 filed on 2019 Jul. 19.

U.S. patent application Ser. No. 16/819,147 was a continuation in part of U.S. patent application Ser. No. 16/598,514 filed on 2019 Oct. 10. U.S. patent application Ser. No. 16/819,147 was a continuation in part of U.S. patent application Ser. No. 15/294,746 filed on 2016 Oct. 16 which issued as U.S. patent Ser. No. 10/627,861 on 2020 Apr. 21. U.S. patent application Ser. No. 16/819,147 claimed the priority benefit of U.S. provisional patent application 62/882,560 filed on 2019 Aug. 4. U.S. patent application Ser. No. 16/819,147 claimed the priority benefit of U.S. provisional patent application 62/820,337 filed on 2019 Mar. 19.

U.S. patent application Ser. No. 16/598,514 was a continuation in part of U.S. patent application Ser. No. 15/294,746 filed on 2016 Oct. 16 which issued as U.S. patent Ser. No. 10/627,861 on 2020 Apr. 21. U.S. patent application Ser. No. 16/598,514 was a continuation in part of U.S. patent application Ser. No. 14/623,337 filed on 2015 Feb. 16 which issued as U.S. Pat. No. 9,582,035 on 2017 Feb. 28. U.S. patent application Ser. No. 15/431,769 was a continuation in part of U.S. patent application Ser. No. 14/623,337 filed on 2015 Feb. 16 which issued as U.S. Pat. No. 9,582,035 on 2017 Feb. 28. U.S. patent application Ser. No. 15/294,746 was a continuation in part of U.S. patent application Ser. No. 14/623,337 filed on 2015 Feb. 16 which issued as U.S. Pat. No. 9,582,035 on 2017 Feb. 28.

U.S. patent application Ser. No. 14/623,337 claimed the priority benefit of U.S. provisional patent application 62/115,691 filed on 2015 Feb. 13. U.S. patent application Ser. No. 14/623,337 claimed the priority benefit of U.S. provisional patent application 62/113,423 filed on 2015 Feb. 7. U.S. patent application Ser. No. 14/623,337 claimed the priority benefit of U.S. provisional patent application 62/111,163 filed on 2015 Feb. 3. U.S. patent application Ser. No. 14/623,337 claimed the priority benefit of U.S. provisional patent application 62/106,856 filed on 2015 Jan. 23. U.S. patent application Ser. No. 14/623,337 claimed the priority benefit of U.S. provisional patent application 62/100,217 filed on 2015 Jan. 6. U.S. patent application Ser. No. 14/623,337 claimed the priority benefit of U.S. provisional patent application 61/948,124 filed on 2014 Mar. 5. U.S. patent application Ser. No. 14/623,337 claimed the priority benefit of U.S. provisional patent application 61/944,090 filed on 2014 Feb. 25.

The entire contents of these related applications are incorporated herein by reference.

FEDERALLY SPONSORED RESEARCH: Not Applicable

SEQUENCE LISTING OR PROGRAM: Not Applicable

BACKGROUND—FIELD OF INVENTION

This invention relates to wrist-worn electronic devices with displays.

INTRODUCTION

Smart watches have several advantages over handheld mobile devices. For example, smart watches can incorporate biometric sensors and are less cumbersome than a cell phone for athletic activities. However, a significant disadvantage of conventional smart watches is their small screen size.

REVIEW OF THE RELEVANT ART

U.S. Pat. No. 7,558,057 (Naksen et al., Jul. 7, 2009, "Personal Digital Device with Adjustable Interface") discloses a personal digital device with a variable-stiffness screen which can vary in size. U.S. patent application publication 20090219788 (Henley, Sep. 3, 2009, "Combination Watch and Cell Phone Foldable onto Each Other for Use Around a Wrist of a User") discloses a combination watch and cell phone which is foldable. U.S. Pat. No. 8,279,716 (Gossweiler et al., Oct. 2, 2012, "Smart-Watch Including Flip Up Display"), U.S. Pat. No. 8,379,488 (Gossweiler et al., Feb. 19, 2013, "Smart-Watch Including Flip Up Display"), and U.S. Pat. No. 8,902,714 (Gossweiler et al., Dec. 2, 2014, "Smart-Watch Including Flip Up Display") disclose a smart-watch with a flip-up portion.

U.S. patent application publication 20130275910 (Kim et al., Oct. 17, 2013, "Optimization of Application Execution Based on Length of Pulled Out Flexible Display Screen") discloses tablets with extension screens. Chinese patent CN203858462U (Feng et al., Dec. 18, 2013, "Dual-Screen Smart Watch") discloses a dual-screen smart watch. U.S. Pat. No. 8,851,372 (Zhou et al., Oct. 7, 2014, "Wearable Personal Digital Device With Changeable Bendable Battery and Expandable Display Used As Standalone Electronic Payment Card") discloses a wearable personal digital device and methods for enlarging its display space. U.S. patent application publication 20150029227 (Park et al., Jan. 29, 2015, "Wrist-Wearable Display Apparatus and Method for Controlling the Same") discloses a smart watch with a rotatable display.

U.S. patent application publication 20150378393 (Erad et al., Dec. 31, 2015, "Mobile Device with Multiple Interconnected Display Units") discloses a phone with an extension screen. U.S. patent application publication 20180120901 (Jin et al., Dec. 31, 2015, "Foldable Display Device and Electronic Apparatus with the Same and Control Method of the Same") discloses a foldable display device with three screens. U.S. patent application publications 20160239190 (Forutanpour et al., Aug. 18, 2016, "Efficient Display of Content on Wearable Displays") and 20160240154 (Forutanpour et al., Aug. 18, 2016, "Efficient Operation of Wearable Displays") disclose a wearable device with a flexible display region which can operate in a wrinkled state.

U.S. patent application publication 20160267310 (Al Nasser et al., Sep. 15, 2016, "Wearable Device") discloses a watch with a bar-code reader and a rotating display. U.S. patent application publication 20180018930 (Pasupathi, Jan.

18, 2018, "Variable Display Size for an Electronic Display Device"), and also U.S. patent Ser. No. 10/319,331 (Pasupathi, Jun. 11, 2019, "Variable Display Size for an Electronic Display Device") and 10755668 (Pasupathi, Aug. 25, 2020, "Variable Display Size for an Electronic Display Device") disclose a device with folding displays which vary in size. U.S. Pat. No. 9,933,756 (Tang, Apr. 3, 2018, "Smart Watch") discloses a smart watch with first and a second displays on the front and a back, respectively, of a shell body.

U.S. patent Ser. No. 10/152,028 (Kim, Dec. 11, 2018, "Wristwatch Type Smart Terminal") discloses a smart watch with bending and rotating screens. PCT WO/2019/084971 (Yang, Sep. 5, 2019, "Double-Screen Smart Watch") discloses a watch with two overlapping screens. U.S. patent application publication 20200042037 (Sun, Feb. 6, 2020, "Wearable Display Device") discloses a wearable display device with a flexible screen and a support component supporting the flexible screen.

SUMMARY OF THE INVENTION

Smart watches have several advantages over handheld mobile devices. For example, smart watches can incorporate biometric sensors and are less cumbersome than a cell phone for athletic activities. However, a significant disadvantage of conventional smart watches is their small screen size. This invention addresses this problem. Disclosed herein are designs for innovative smart watches with variable-configuration displays which combine to provide the wearer with a larger combined display when needed.

When a person wearing one of these innovative smart watches does not need a large display area, then a plurality of displays on the watch fit around the person's wrist and/or arm in a relatively compact first configuration. The displays in this first configuration do not restrict movement of the person's wrist, are not likely to be snagged on an external object, and are not very bulky looking. When the person needs a larger display area, then the plurality of displays are moved into a second configuration which creates a large, coplanar, combined display. When these displays are touch screens, then the combined display can serve as a larger user interface than is possible with a conventional smart watch.

DETAILED DESCRIPTION OF THE FIGURES

Figure 1:
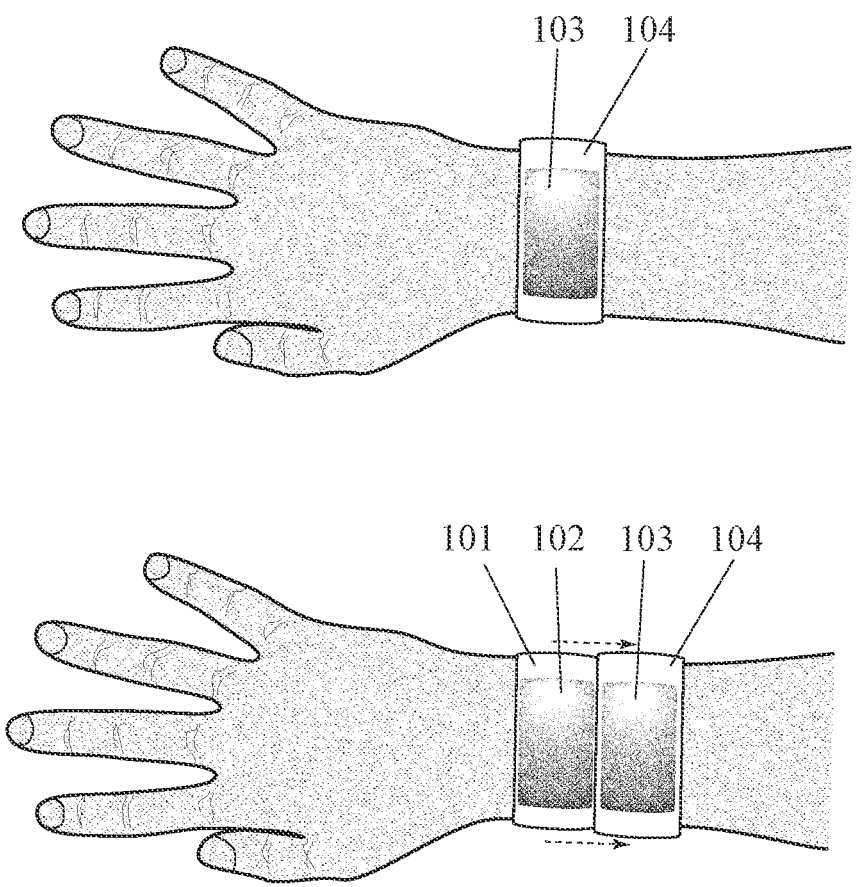
FIG. 1 shows a wrist-worn device with a portion which slides over to uncover two displays instead of one.

FIG. 1 shows views at two different times of an example of a wearable computing device for the wrist and/or arm comprising: a first attachment member 101, wherein the first attachment member is a band (e.g. band, strap, bracelet, or sleeve) which is attached to (e.g. encircles or goes around) a person's wrist and/or arm; a first display (e.g. display screen and/or touch screen) 102 on the first attachment member; a second attachment member 103 which is movably connected to the first attachment member; and a second display (e.g. display screen and/or touch screen) 104 on the second attachment member; wherein the device is moved from a first configuration to a second configuration by sliding the second attachment member and/or the second display in a proximal direction (e.g. parallel to the longitudinal axis of the person's forearm and/or perpendicular to the plane of the circumference of the first attachment member). The upper portion of FIG. 1 shows this device in the first configuration. The lower portion of FIG. 1 shows this device in the second configuration.

In the second configuration, the first and second displays combine to form a larger combined display area. The device can be kept in the more-compact first configuration when a larger display area is not needed and can be temporarily moved into the second configuration when a larger display area is needed. In an example, the device can be moved manually from the first configuration to the second configuration, or vice versa, by the person wearing the device. In an example, the device can be moved automatically from the first configuration to the second configuration, or vice versa, by an actuator in the device. In an example, automatic movement of a display from the first configuration to the second configuration, or vice versa, can be triggered by one or more events selected from the group consisting of: body motion detected by a sensor in the device; an incoming communication; type of content displayed; a touch detected by a sensor in the device; and a voice command.

In an example, the second attachment member can overlap the first attachment member in the first configuration and not overlap the first attachment member in the second configuration. In an example, the second attachment member can be parallel to the first attachment member in the first configuration and be coplanar with (and adjacent to) the first attachment member in the second configuration. In an example, the first and second attachment members can be concentric and/or nested in the first configuration and adjacent to each other in the second configuration. In an example, the second display can overlap the first display in the first configuration and not overlap the first display in the second configuration. In an example, the second display can be parallel to the first display in the first configuration and be coplanar with (and adjacent to) the first display in the second configuration. In an example, the first and second displays can be concentric and/or nested in the first configuration and adjacent to each other in the second configuration.

In an example, a second attachment member can cover a first display in the first configuration. In an example, first and second displays can be stacked in the first configuration. In an example, sliding a second attachment member from a first configuration to a second configuration can uncover the first display. In an example, only the second display of the two displays may be visible to the person when a device is in a first configuration, but both first and second displays can be visible to the person when the device is in a second configuration. In an example, a first display can be activated (e.g. using power and displaying an image) only in a second configuration. In an example, a first display can be automatically deactivated (e.g. no power used or image displayed) when a device is moved into in a first configuration.

In an example, a first display can have a longitudinal shape (e.g. rectangle or oval) with a longitudinal axis which is substantially parallel to the plane of the circumference of a band. In an example, a second display can have a longitudinal shape (e.g. rectangle or oval) with a longitudinal axis which is substantially parallel to the plane of the circumference of a band. In an example, both first and second displays can have longitudinal shapes (e.g. rectangles or ovals) with longitudinal axes which are substantially parallel to the plane of the circumference of a band.

In an example, a second attachment member can be locked (e.g. locked, latched, snapped, clipped, or magnetically attached) into place in a second configuration, but can also be subsequently unlocked by the wearer so that it can slide back into a first configuration. In an example, a second display can be reversibly attached (e.g. locked, latched, snapped, clipped, or magnetically attached) to a first display in a second configuration. In an example, a device can further comprise press buttons (or tabs) on the lateral (e.g. right or left) sides of a second attachment member, wherein the wearer presses these buttons (or tabs) to lock (or unlock) the second attachment member into (or out of) its first and/or second configurations.

In an example, a second attachment member can be held in place in the second configuration by a tensile element (e.g. a spring or elastic element) so that it can remain generally in place, but can still bend as needed if the wearer moves (e.g. twists or flexes) their wrist and/or arm or the device is bumped by an external object. In an example, first and second attachment members can be connected by a flexible, spring-loaded joint or hinge so that they can bend and/or flex relative to each other when the second attachment member is extended out from the first attachment member. This can help to avoid injury to the person's skin and/or breakage of the device if the person bends or twists their arm when the second attachment member is extended.

In an example, there can be proximal-to-distal tracks (e.g. tracks, guides, or slots) on the lateral (e.g. right and left) sides of the first display and/or a housing for the first display, wherein the second attachment member is connected to the first attachment member along these tracks and slides along these tracks as it moves from the first configuration to the second configuration, or vice versa. In an example, the lateral (e.g. right and left) sides of the second attachment member can extend out more than the lateral sides of the first attachment member, with interdigitated proximal-to-distal tracks which movably connect the lateral sides of the first and second attachment members to each other.

In an example, the first display and/or the second display can have a shape selected from the group consisting of: square, rectangle, conic section, hexagon, polygon with rounded vertexes, circular, oval, and oblong. In an example, the second display can be parallel to the first display in the first configuration. In an example, the second display can be on top of (e.g. over or cover up) the first display in the first configuration, but not in the second configuration. In an example, curvature of the second display can be parallel to the curvature of the first display in the first configuration. In an example, the radius of a curved second display can be larger than the radius of a curved first display. In an example, the radius of a curved second display can be smaller than the radius of a curved first display. In an example, first and second displays can be nested and/or concentric relative to each other. In an example, the second display can be farther from the person's body than the first display. In an example, the second display can be closer to the person's body than the first display.

In an example, the first and second displays can be the same size. In an example, the first display can have a proximal-to-distal width in the range of 1.5" to 2". In an example, the first display can have a proximal-to-distal width in the range of 1" to 3". In an example, the first display can have a lateral (e.g. right to left) length in the range of 1.5" to 4". In an example, the second display can have a proximal-to-distal width in the range of 1.5" to 2". In an example, the second display can have a proximal-to-distal width in the range of 1" to 3". In an example, the second display can have a lateral (e.g. right to left) length in the range of 1.5" to 4".

In an example, the second attachment member can be flat and parallel to the first attachment member in the first configuration. In an example, the second attachment member can be curved and the curvature of the second attachment member can be parallel to the curvature of the first attachment member in the first configuration. In an example, the radius of a curved second attachment member can be larger than the radius of a curved first attachment member. In an example, the radius of a curved second attachment member can be smaller than the radius of a curved first attachment member. In an example, first and second attachment members can be nested and/or concentric relative to each other. In an example, the first attachment member spans (e.g. encircles) the entire circumference of the person's wrist and/or arm, but the second attachment member only spans between 25% and 75% of the circumference of the person's wrist and/or arm.

In an example, there can be a flexible and/or expandable sheet or layer between the second attachment member and the person's body. This can help avoid pinching the person's skin as the second attachment member is moved. In an example, a flexible and/or expandable sheet or layer can uncoil or coil between the second attachment member and the person's body as the device is moved from the first configuration to the second configuration. In an example, a flexible and/or expandable sheet or layer can roll out or roll up between the second attachment member and the person's body as the device is moved from the first configuration to the second configuration. In an example, a flexible and/or expandable sheet or layer can be elastic and stretch out or contract as the device is moved from a first configuration to a second configuration.

In an example, there can be one or more interdigitated tracks (e.g. tracks, ridges, guides, and/or bearings) which connect the first and second attachment members. In an example, a second attachment member can slide along these one or more tracks relative to the first attachment member. In an example, there can be one track on one side (e.g. to the right) of the first display and one track on the other side (e.g. to the left) of the first display. In an example, a second attachment member can be attached to a first attachment member by one or more moving rods, tubes, bars, or pins. In an example, a second attachment member can be attached to a first attachment member by two or more telescoping rods, tubes, bars, or pins.

In an example, a second attachment member can slide laterally along the surface of the wrist and/or arm and also move closer to the surface of the wrist and/or arm as it moves from the first to the second configuration, so that the second display becomes coplanar with the first display in the second configuration. In an example, a second attachment member can slide between 1" and 3" laterally along the surface of the wrist and/or arm and also move less than ½" closer to the surface of the wrist and/or arm as it moves from the first to the second configuration, so that the second display becomes coplanar with the first display in the second configuration. In an example, a second attachment member can be attached to a first attachment member by a non-linear track and/or hinge mechanism which moves the second attachment member closer to the surface of the person's arm or wrist as it moves from the first configuration to the second configuration.

In an example, the first attachment member can span the entire circumference of the person's wrist and/or arm, but the second attachment member only spans between 25% and 75% of the circumference of the person's wrist and/or arm. In an example, the first attachment member can span the entire circumference of the person's wrist and/or arm, but the second attachment member only spans half of the person's wrist and/or arm. In an example, the first attachment member can span the entire circumference of the person's wrist and/or arm, but the second attachment member spans less than half of the person's wrist and/or arm. In an example, a second attachment member can span half of the circumference of the person's wrist and/or arm, including the dorsal side of the person's wrist and/or arm. In an example, a second attachment member can span a quarter of the circumference of the person's wrist and/or arm, including the dorsal side of the person's wrist and/or arm.

In an example, first and second displays can show different images and/or serve different interface functions. In an example, one display can show an image of the wearer and the other display can show an image of a person with whom the wearer is communicating. In an example one display can show an image and the other display can show text or a control pad. In an example, the one display can display a summary of the information which is displayed in more detail on other displays. In another example, the two displays can show two portions of the same image. In an example, the two displays can combine to form a single larger display in the second configuration.

In an example, a display can display information with a proximal-to-distal or distal-to-proximal orientation. In an example, a display can display information with a lateral orientation. In an example, the device can automatically change the orientation of information on a display based on the orientation and/or movement of the device as detected by a gyroscope and/or motion sensor which is incorporated into the device. In an example, the orientation of information on a display can be automatically changed based on the orientation and/or position of the device relative to the person's eyes. In an example, the orientation and/or position of the device relative to the person's eyes can be determined based on data from one or more cameras, motion sensors, inertial sensors, and/or bend sensors which are incorporated into the device.

In an example, the device can further comprise one or more sensors selected from the group consisting of: accelerometer, blood pressure sensor, camera or other imaging sensor, electrocardiogram (ECG) sensor, electrochemical sensor, electrogoniometer, electromyography (EMG) sensor or other electromagnetic sensor, optoelectronic sensor, galvanic skin response (GSR) sensor, glucose sensor, gyroscope, heart rate sensor, inclinometer, infrared light sensor, ultraviolet light sensor, makesnosensor, microphone or other sound sensor, neurosensor, motion sensor, piezoelectric sensor, pressure sensor, blood oximetry sensor, spectroscopic sensor or other light-spectrum-analyzing sensor, strain gauge, ultrasonic sensor, MEMS sensor, GPS sensor, compass, magnetometer, humidity sensor, food consumption detector, and temperature sensor.

In an example, a sensor can be a multi-axial accelerometer. In an example, a sensor can be a gyroscope. In an example, a sensor can be a light energy sensor. In an example, a sensor can be a spectroscopic sensor which collects data concerning the spectrum of light reflected from and/or transmitted through tissue of the person's wrist and/or forearm. In an example, a sensor can be an electromagnetic energy sensor. In an example, a sensor can measure the resistance, impedance, and/or conductivity of tissue of the person's wrist and/or forearm with respect to the transmission of electromagnetic energy. In an example, a sensor can measure electromagnetic energy emitted from muscles and/or nerves in the person's wrist and/or forearm. In an example, a sensor can be a capacitive electromagnetic energy sensor.

In an example, a sensor can be an environmental light energy sensor. In an example, a display can have a first display mode which requires less energy and a second display mode which requires more energy. In an example, a display can automatically switch from the first display mode to the second display mode when the second display mode is required for the person to be able to see information on the display. In an example, the device can switch the display from the first mode to the second mode when there is a high level of environmental light energy and the display would not be visible in bright light in the first display mode. In an example, the device can switch the display from the first mode to the second mode when there is a low level of environmental light energy and the display would not be visible in dim light (or darkness) in the first display mode.

In an example, a device can change one or more displays from a first (lower energy) display mode to a second (higher energy) display mode, or vice versa, based on data from one or more motion and/or inertial sensors which are incorporated into the device or with which the device is in wireless communication. In an example, when a motion and/or inertial sensor indicates a first level of movement of the device or a first orientation of the device, then the assumption is that the person is not looking at the device and the device sets the display to the first (lower energy) display mode. In an example, when a motion and/or inertial sensor indicates a second level of movement of the device or a second orientation of the device, then the assumption is that the person may be looking at the device and the device sets the display to the second (higher energy) display mode.

In an example, a device can be part of a multi-device system which includes other locations on a person's body, such as the person's head or torso. In an example, this device can be in communication with a motion and/or inertial sensor which is located elsewhere on the person's body so that the relative motion or relative orientation of the device (relative to the rest of the person's body) can be monitored. Measuring the relative motion or orientation of the device (e.g. relative to the rest of the person's body) rather than absolute motion or position of the device (e.g. relative to the earth) can help to factor out changes in motion or orientation which are due to being in a car, elevator, or airplane. Even though the absolute position or orientation of a device might be changing rapidly in a car, elevator, or airplane, the relative position of the device (relative to the rest of the person) may be stable and the person may wish see the display.

In an example, a device can further comprise one or more components selected from the group consisting of: a data processor, a data transmitter, a data receiver, a power source, and an energy harvester. In an example, a device can communicate with a handheld electronic device, a different wearable technology device, an array of wearable sensors, a communication network tower, a satellite, a home control system, and/or an implantable medical device. In an example, a device can further comprise one or more components selected from the group consisting of: one or more LEDs; one or more coherent light emitters or projectors; one or more infrared light emitters or projectors; one or more sound-emitting members; one or more tactile-sensation-creating members; one or more neurostimulators, myostimulators, or other electromagnetic energy emitters; one or more hardware buttons, knobs, or keys, a virtual projected keypad; a gesture-recognition interface; a speech-recognition interface, and an eye-gaze-tracking interface. Other example variations discussed in this disclosure or in priority-linked disclosures can also be applied to this example where relevant.

Figure 2:
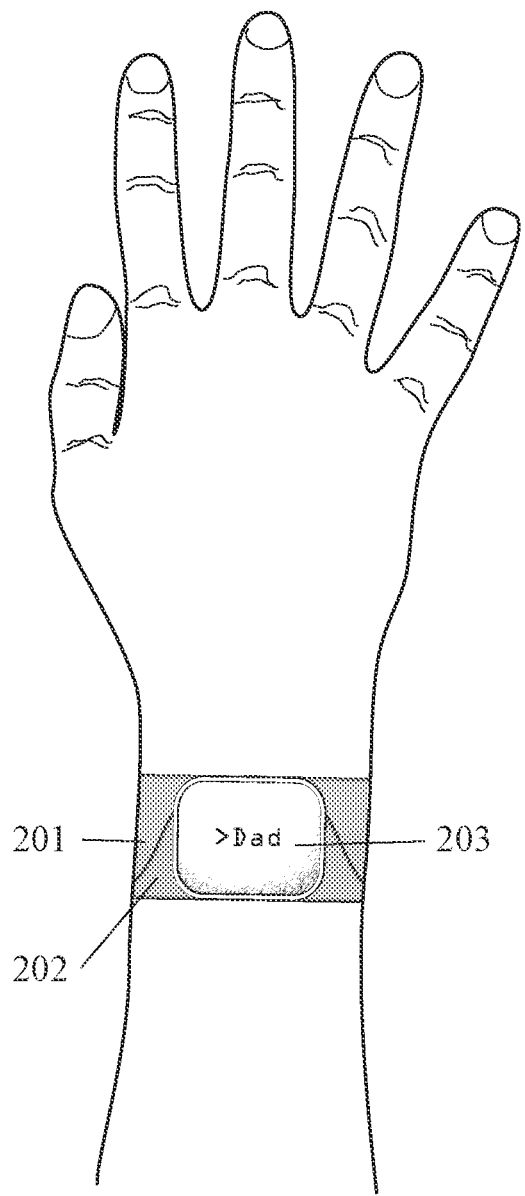
FIGS. 2 and 3 show a wrist-worn device with a part which flips over to uncover two displays instead of one.
Figure 3:
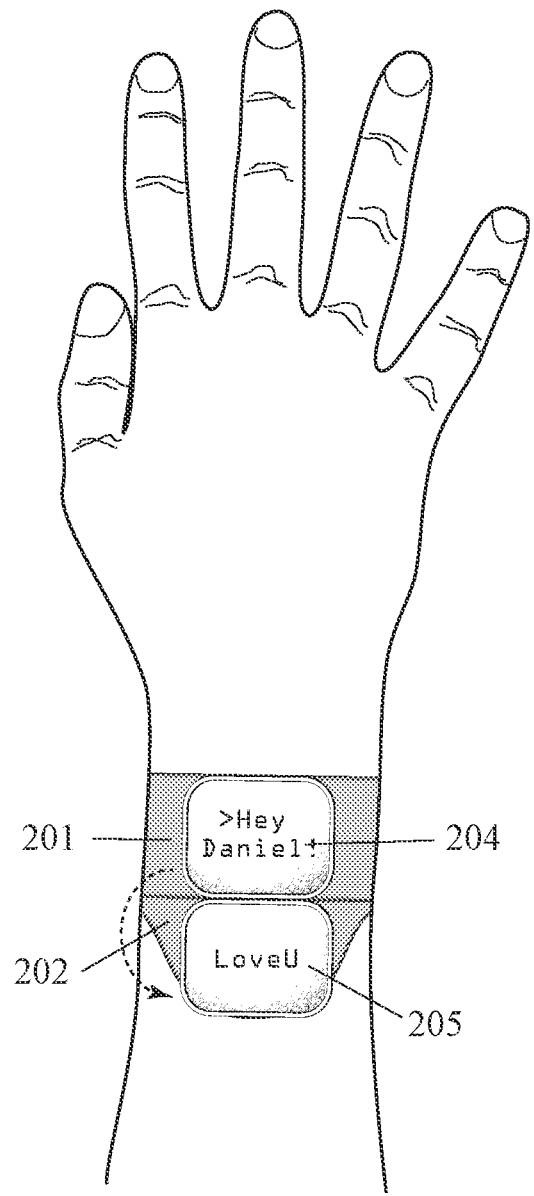

FIGS. 2 and 3 show views at two different times of a wearable computing device for the wrist and/or arm comprising: a primary band or strap 201 which is attached to a person's wrist and/or forearm; a secondary band or strap 202 which is connected to the primary band or strap by a flexible joint, hinge, or fold wherein the secondary band or strap has a first configuration which overlaps the primary band or strap by a first amount, wherein the secondary band or strap has a second configuration which overlaps the primary band or strap by a second amount (or not at all), wherein the second amount is less than the first amount, and wherein the secondary band or strap is moved from the first configuration to the second configuration by unfolding, rotating, pivoting, or flipping the secondary band or strap around the joint, hinge, or fold; a first display 203 on the secondary band or strap, wherein the first display is only visible to the person when the secondary band or strap is in the first configuration; a second display 204 on the primary band or strap, wherein the second display is only visible to the person when the secondary band or strap is in the second configuration; and a third display 205 on the secondary band or strap, wherein the third display is only visible to the person when the secondary band or strap is in the second configuration.

FIG. 2 shows the device in the first configuration. FIG. 3 shows the device in the second configuration. The device can be kept in the first configuration, which is more compact, when the person does not need a larger display area, but can be reversibly moved into the second configuration when the person needs a larger display area. In an example, the combined display area can be at least twice as large in the second configuration as in the first configuration. Movement of the secondary strap or band from the first to second configurations is symbolically-represented by a dotted-line arrow.

In an example, a secondary band or strap can be moved from a first configuration to a second configuration by being unfolded, rotated, pivoted, and/or flipped around a side-to-side (e.g. right side to left side) axial joint, hinge, or fold which connects the secondary band or strap to the primary band or strap. In an example, there can be an axial joint, hinge, or fold along the surface of a person's wrist and/or forearm and an edge of a secondary band or strap which is opposite to the axial joint, hinge, or fold is rotated away from the surface of the wrist and/or forearm during the transition from the first configuration to the second configuration. In an example, a secondary band or strap can be moved manually (e.g. by the person wearing the device) from the first configuration to the second configuration. In another example, a secondary band or strap can be moved automatically from the first configuration to the second configuration by an actuator which is part of the device.

In this example, the first display faces away from the surface of the person's wrist and/or arm in the first configuration and faces toward the surface of person's wrist when the device is in the second configuration. In this example, the second display faces away from the surface of the person's wrist and/or arm in both the first configuration and in the second configuration, but is obscured from view by the secondary band or strap in the first configuration. In this example, the third display faces toward the surface of the person's wrist and/or arm in the first configuration and faces away from the surface of the person's wrist and/or arm in the second configuration. In an example, the first display (on the secondary band or strap) is only activated (e.g. using power and showing an image) in the first configuration. In an example, the second display (on the primary band or strap) and the third display (on the secondary band or strap) are only activated (e.g. using power and showing an image) in the second configuration.

In an example, the device can be said to have been "flipped open" when the secondary band or strap has been moved from the first configuration to the second configuration. In an example, the secondary band or strap can completely overlap the primary band or strap in the first configuration and not overlap the primary band or strap at all in the second configuration. In an example, the secondary band or strap can lie flat against the surface of the person's wrist and/or forearm in the second configuration. In an example, the secondary band or strap "flips open" in a proximal direction—moving closer to the person's elbow in the transition from the first configuration to the second configuration. In another example, the secondary band or strap can "flip open" in a distal direction—moving away from the person's elbow in the transition from the first configuration to the second configuration.

In an example, a secondary band or strap can be a flexible and/or elastic band, strap, or protrusion which spans less of the circumference of the person's wrist and/or forearm than is spanned by the primary band or strap. In an example, a secondary band or strap can span only the upper (or frontal) surface of the person's wrist and/or arm. In an example, a primary band or strap can span the entire circumference of the person's wrist and/or arm, but the secondary band or strap only spans between 25% and 75% of the circumference of the person's wrist and/or arm. In an example, a primary band or strap can span the entire circumference of the person's wrist and/or arm, but the secondary band or strap only spans between 20% and 50% of the circumference of the person's wrist and/or arm.

In an example, first, second, and third displays can be the same size. In an example, a display can have a proximal-to-distal width in the range of 1.5" to 2". In an example, a can have a proximal-to-distal width in the range of 1" to 3". In an example, a display can have a proximal-to-distal width in the range of 0.05 to 0.20 cubits. In an example, a display can have a lateral (e.g. right to left) length in the range of 1.5" to 4". In an example, a display can have image-display area in the range of 1 to 6 square inches.

As shown in FIGS. 2 and 3, a secondary band or strap can have arcuate edges which connect it to the lateral sides of the third display. In an example, there can be arcuate elastic connections between the third display and the primary band or strap. In an example, a secondary band or strap can have a sinusoidal, undulating, or other arcuate wave shape. As shown in FIGS. 2 and 3, a secondary band or strap can further comprise two arcuate (e.g. half-parabolic) sections, one half-parabolic section between the right side of the third display and the primary band or strap and one half-parabolic section between the left side of the third display and the primary band or strap. These arcuate edges, connections, and/or sections can reduce the chances of the third display snagging on something when the device is in the second configuration and the display is extended.

In an example, at least 75% of a secondary band or strap overlaps a primary band or strap in the first configuration. In an example, at least 90% of a secondary band or strap overlaps a primary band or strap in the first configuration. In an example, a secondary band or strap can completely overlap a primary band or strap in the first configuration. In an example, less than 75% of the secondary band or strap overlaps the primary band or strap in the second configuration. In an example, less than 10% of the secondary band or strap overlaps the primary band or strap in the second configuration. In an example, the secondary band or strap may not overlap the primary band or strap at all in the second configuration.

In an example, a secondary band or strap can be connected to a primary band or strap by a side-to-side (e.g. right side to left side) or lateral axial joint, hinge, or fold. In an example, the surface area of a person's wrist or arm which is covered by the device can be increased when the secondary band or strap is moved from the first configuration to the second configuration. This enables the outward-facing surface of the device to be smaller when only the first display is in use and larger when the second and third displays are in use. In an example, the secondary band or strap can be parallel to the plane of the primary band or strap in the first configuration. In an example the secondary band or strap can be parallel to the plane of the primary band or strap in both the first configuration and second configuration. In an example, the secondary band or strap may temporarily not be parallel to the plane of the primary band or strap during the transition from the first configuration to the second configuration. In an example, the first display and the second display can overlap each other in the first configuration and be coplanar in the second configuration.

In an example, a display can be a computer display screen. In an example, a display can have a cross-sectional shape which is selected from the group consisting of: rectangular with rounded vertexes, hexagonal with rounded vertexes, square, rectangular, hexagonal, circular, elliptical, and oblong. In an example, the second and third displays can be centrally aligned along the same proximal-to-distal axis of the person's wrist and/or forearm. In an example, a display can have a flat display surface. In an example, a display can be a touch screen which responds to finger movements. In this example, the first, second, and third displays are separate components. In another example, the first and third displays can be top and bottom views of the same component. In another example, the device may not have a first display and only have the second and third displays.

In an example, the first display can display a summary of the information which is displayed in more detail on the second and third displays. In an example, the second and third displays can display two different sections of the same text content. In an example, the second and third displays can display two different sections of the same image content. In an example, the second and third displays can display text and image, respectively, from the same multi-media content. In an example, two of the displays can show two portions of the same image. In an example, two of the displays can combine to form a single larger display in the second configuration.

In an example, a display can display information with a proximal-to-distal or distal-to-proximal orientation. In an example, a display can display information with a lateral orientation. In an example, the device can automatically change the orientation of information on a display based on the orientation and/or movement of the device as detected by a gyroscope and/or motion sensor which is incorporated into the device. In an example, the orientation of information on a display can be automatically changed based on the orientation and/or position of the device relative to the person's eyes. In an example, the orientation and/or position of the device relative to the person's eyes can be determined based on data from one or more cameras, motion sensors, inertial sensors, and/or bend sensors which are incorporated into the device.

In an example, a forearm-wearable device can further comprise one or more sensors. In an example, a sensor can be a multi-axial accelerometer. In an example, a sensor can be a gyroscope. In an example, a sensor can be a light energy sensor. In an example, a sensor can be a spectroscopic sensor which collects data concerning the spectrum of light reflected from and/or transmitted through tissue of the person's wrist and/or forearm. In an example, a sensor can be an electromagnetic energy sensor. In an example, a sensor can measure the resistance, impedance, and/or conductivity of tissue of the person's wrist and/or forearm with respect to the transmission of electromagnetic energy. In an example, a sensor can measure electromagnetic energy emitted from muscles and/or nerves in the person's wrist and/or forearm. In an example, a sensor can be a capacitive electromagnetic energy sensor.

In an example, a sensor can be an environmental light energy sensor. In an example, a display can have a first display mode which requires less energy and a second display mode which requires more energy. In an example, a display can automatically switch from the first display mode to the second display mode when the second display mode is required for the person to be able to see information on the display. In an example, the device can switch the display from the first mode to the second mode when there is a high level of environmental light energy and the display would not be visible in bright light in the first display mode. In an example, the device can switch the display from the first mode to the second mode when there is a low level of environmental light energy and the display would not be visible in dim light (or darkness) in the first display mode.

In an example, this device can change one or more displays from a first (lower energy) display mode to a second (higher energy) display mode, or vice versa, based on data from one or more motion and/or inertial sensors which are incorporated into the device or with which the device is in wireless communication. In an example, when a motion and/or inertial sensor indicates a first level of movement of the device or a first orientation of the device, then the assumption is that the person is not looking at the device and the device sets the display to the first (lower energy) display mode. In an example, when a motion and/or inertial sensor indicates a second level of movement of the device or a second orientation of the device, then the assumption is that the person may be looking at the device and the device sets the display to the second (higher energy) display mode.

In an example, this device can be part of a multi-device system which includes other locations on a person's body, such as the person's head or torso. In an example, this device can be in communication with a motion and/or inertial sensor which is located elsewhere on the person's body so that the relative motion or relative orientation of the device (relative to the rest of the person's body) can be monitored. Measuring the relative motion or orientation of the device (e.g. relative to the rest of the person's body) rather than absolute motion or position of the device (e.g. relative to the earth) can help to factor out changes in motion or orientation which are due to being in a car, elevator, or airplane. Even though the absolute position or orientation of a device might be changing rapidly in a car, elevator, or airplane, the relative position of the device (relative to the rest of the person) may be stable and the person may wish see the display. Other example variations discussed in this disclosure or in priority-linked disclosures can also be applied to this example where relevant.

FIGS. 4 through 7 show four views, from two different angles and at two different times, of an example of a wearable computing device for the wrist and/or arm comprising: a distal band around a person's wrist and/or forearm, wherein the distal band has a narrow portion and a wide portion; a proximal band around the person's wrist and/or forearm, wherein the proximal band has a narrow portion and a wide portion, wherein the distal band and the proximal band have a first configuration in which the narrow portion of the distal band is aligned with (e.g. adjacent to or along-side) the wide portion of the proximal band, wherein the distal band and the proximal band have a second configuration in which the wide portion of the distal band is aligned with (e.g. adjacent to or along-side) the wide portion of the proximal band, and wherein the distal band and the proximal band are moved from the first configuration to the second configuration by rotation of one band around the wrist and/or arm relative to the other band; a distal display on the wide portion of the distal band; and a proximal display on the wide portion of the proximal band.

Figure 4:
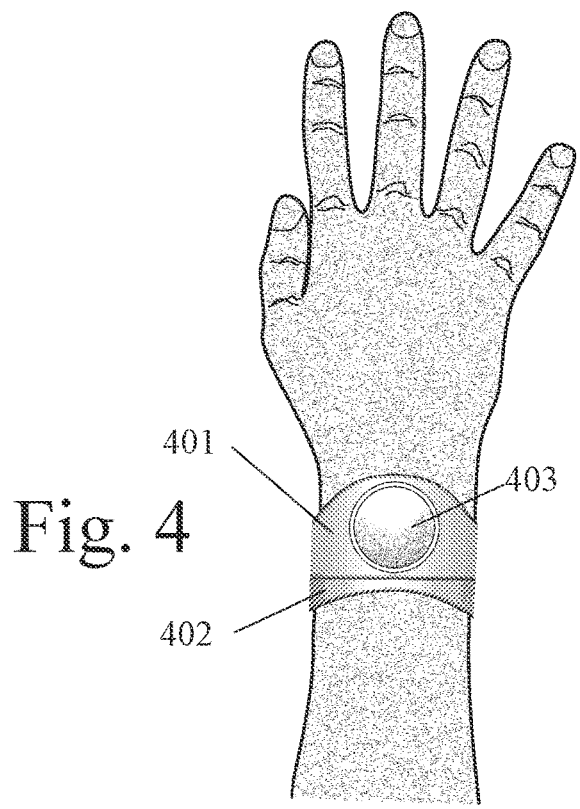
FIGS. 4 through 7 show a wrist-worn device with two bands which are rotated relative to each other to align two circular displays.
Figure 5:
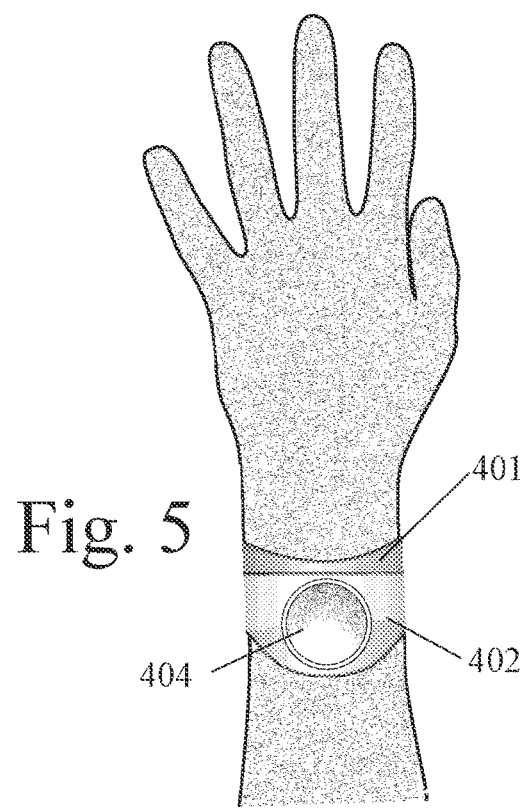
Figure 6:
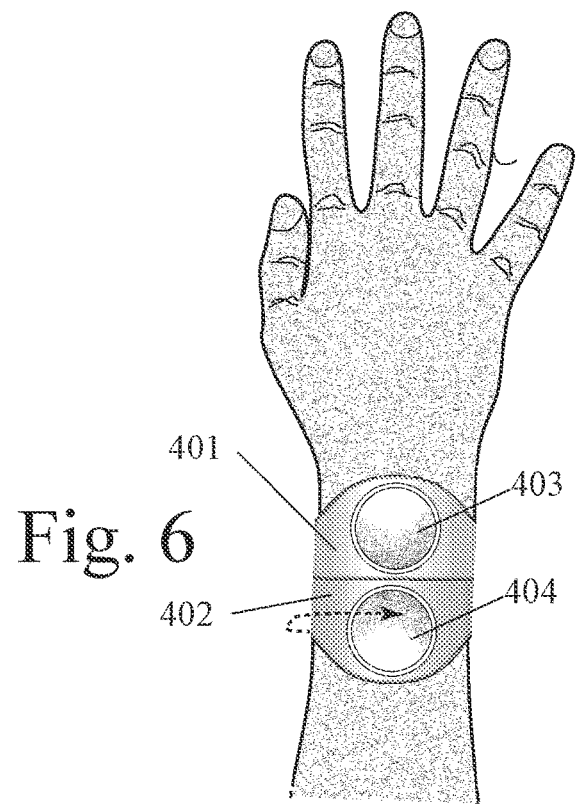
Figure 7:
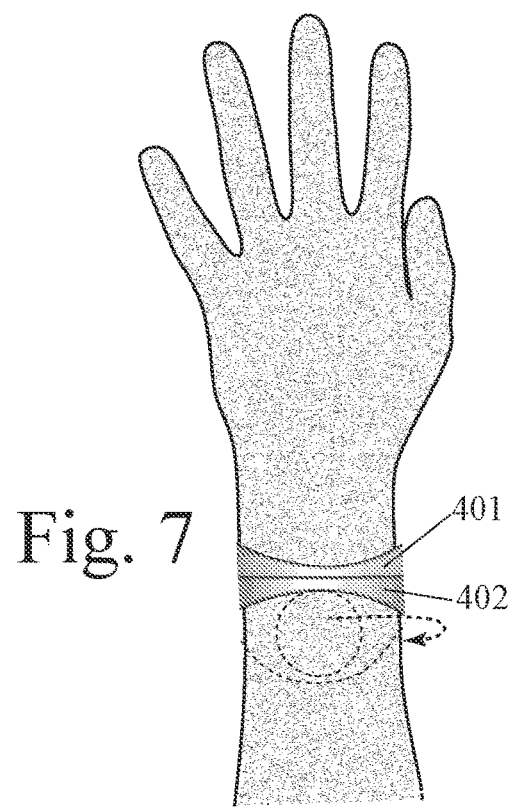

FIGS. 4 and 5 show this device at a first point in time wherein the distal attachment member and the proximal attachment member are in the first configuration. FIG. 4 shows this device from a top-down (frontal) perspective—on the top of the person's wrist and/or forearm. FIG. 5 shows this device from a bottom-up (dorsal) perspective—on the bottom of the person's wrist and/or forearm. FIGS. 6 and 7 show this device at a second point in time, after the distal attachment member and the proximal attachment member have been moved into the second configuration. This movement is symbolically represented by dotted-line arrows. FIG. 6 shows this device from a top-down (frontal) perspective—on the top of the person's wrist and/or forearm. FIG. 7 shows this device from a bottom-up (dorsal) perspective—on the bottom of the person's wrist and/or forearm.

In the first configuration, shown in FIGS. 4 and 5, the wide portion of the distal attachment member is on the top of the person's wrist and/or forearm and the wide portion of the proximal attachment member is on the bottom of the person's wrist and/or forearm. The device can be put in this first configuration to minimize its size as seen from the top when large-scale viewing (e.g. viewing both displays) is not needed. This design can help the device to be relatively unobtrusive (in this first configuration) when large-scale viewing (e.g. viewing both displays) is not needed.

In the second configuration, shown in FIGS. 6 and 7, the proximal attachment member has been rotated so that the wide portions of the distal and proximal attachment members are both on the top of the person's wrist and/or forearm, as well as both displays. The device can be put in this second configuration to maximize large-scale viewing (e.g. viewing both displays) when this is needed. The device is temporarily more obtrusive (in this second configuration) when large-scale viewing (e.g. viewing both displays) is needed. When large-scale viewing is no longer needed, then the device can be rotated back into the first (less obtrusive) configuration.

In the first configuration, the device has a more-uniform width around the circumference of the person's wrist and/or arm, so that it does not restrict arm movement very much and is unlikely to be caught on an external object. In the second configuration, the device provides a larger (potentially twice as large) combined display area on a particular side (e.g. the dorsal side) of the person's wrist and/or forearm. The device can be moved into the first configuration when a larger combined display area is not needed and can be moved into the second configuration when a larger combined display area is needed.

With respect to specific components, FIGS. 4 through 7 show four views, from two different angles and at two different times, of an example of a wearable computing device for the wrist and/or arm comprising: a distal attachment member 401 (such as a strap or band) which is configured to span the circumference of the person's wrist and/or forearm, wherein the distal attachment member has a narrow portion of its circumference and a wide portion of its circumference; a proximal attachment member 402 (such as a strap or band) which is configured to span the circumference of the person's wrist and/or forearm, wherein the proximal attachment member further has a narrow portion of its circumference and a wide portion of its circumference, wherein the distal attachment member and the proximal attachment member have a first configuration in which the narrow portion of the distal attachment member is aligned with (e.g. adjacent to or along-side) the wide portion of the proximal attachment member, wherein the distal attachment member and the proximal attachment member have a second configuration in which the wide portion of the distal attachment member is aligned with (e.g. adjacent to or along-side) the wide portion of the proximal attachment member, and wherein the distal attachment member and the proximal attachment member are moved from the first configuration to the second configuration by the rotation of one attachment member around the wrist and/or arm relative to the other attachment member; a distal display 403 which is attached to, or part of, the wide portion of the distal attachment member; and a proximal display 404 which is attached to, or part of, the wide portion of the proximal attachment member.

The wearable computing device for the wrist and/or arm shown in FIGS. 4 through 7 can also be described as comprising: a distal band which is configured to span a circumference of a person's wrist and/or forearm, wherein the distal band has a circumference with a narrow portion and a wide portion; a proximal band which is configured to span the circumference of the person's wrist and/or forearm; wherein the proximal band has a circumference with a narrow portion and a wide portion; wherein the distal band and the proximal band have a first configuration in which the narrow portion of the distal band is aligned with the wide portion of the proximal band; wherein the distal band and the proximal band have a second configuration in which the wide portion of the distal band is aligned with the wide portion of the proximal band; and wherein the distal band and the proximal band are moved from the first configuration to the second configuration by rotation of the distal band around the wrist and/or arm relative to the proximal band, or vice versa; a distal display on the wide portion of the distal band; and a proximal display on the wide portion of the proximal band.

In an example, a proximal attachment member and a distal attachment member can be moveably connected to each other by a track or ridge which encircles the person's wrist and/or arm. In an example, a proximal attachment member and a distal attachment member can be movably connected to each other by interdigitated tracks or ridges. In an example, a proximal attachment member and a distal attachment member can be movably connected to each other by ball bearings. In an example, the distal edge of the proximal attachment member can fit into (and slide along) a circumferential track or ridge on the proximal edge of the distal attachment member. In an example, the proximal edge of the distal attachment member can fit into (and slide along) a circumferential track or ridge on the distal edge of the proximal attachment member.

In an example, there can be protective fabric strip, ring, or layer between the device and the person's skin where the proximal and distal attachment members are movably connected so that the person's skin is not caught or pinched when the proximal and/or distal attachment members are moved relative to each other. In an example, the circumference and/or tightness of the device can be automatically adjusted when proximal and/or distal attachment members are moved relative to each other. In an example, the device can be temporarily loosened during movement from the first configuration to the second configuration, or vice versa, and then re-tightened after the movement is completed.

In an example, an attachment member can be a bracelet, armlet, bangle, coil, band, strap, chain, or cuff. In an example, the ends of an attachment member can be attached around a person/s wrist and/or forearm by a buckle, clasp, clip, hook, hook-and-eye material, pin, latch, button, and/or zipper. In an example, an attachment member can be slipped over a person's hand to fit around a person/s wrist and/or forearm. In an example, the distal attachment member can be attached to the proximal attachment member by a sliding track and/or bearings which enable the proximal attachment member to rotate around the wrist and/or forearm relative to the distal attachment member, or vice versa.

In an example, the maximum width of a narrow portion of an attachment member can be in the range of ¼" to 1". In an example, the maximum width of a wide portion of an attachment member can be in the range of ¾" to 4". In an example, the outer edge of an attachment member can have an arcuate shape. In an example, the outer edge of an attachment member can have an undulating or sinusoidal shape. In an example, the outer edges of proximal and distal attachment members can have sinusoidal curve shapes and when their wide portions are aligned, then the curves of their sinusoidal edges are 180-degrees out of phase with each other. In an example, the outer edges of proximal and distal attachment members can have sinusoidal curve shapes and when they are in the second configuration, then the curves of their sinusoidal edges are 180-degrees out of phase with each other. In an example, the outer edges of proximal and distal attachment members can have sinusoidal curve shapes and when they are in the first configuration, then the curves of their sinusoidal edges are in phase with each other.

In an example, proximal and distal displays can both be circular in shape. In an example, the centers of circular proximal and distal displays can be aligned, along a common proximal-to-distal axis, in the second configuration. In an example, proximal and distal displays can both be quadrilateral in shape. In an example, the centers of quadrilateral proximal and distal displays can be aligned, along a common proximal-to-distal axis, in the second configuration, but not in the first configuration. In an example, an edge of a proximal display and an edge of a distal display can be aligned, adjacent, and/or contiguous with each other in the second configuration, but not in the first configuration.

In an example, a display can be a computer screen. In an example, a display can have a cross-sectional shape which is selected from the group consisting of: rectangular with rounded vertexes, hexagonal with rounded vertexes, square, rectangular, hexagonal, circular, elliptical, and oblong. In an example, two displays can be centrally aligned along the same proximal-to-distal axis of the person's wrist and/or forearm. In an example, a display can have a flat display surface. In an example, a display can be a touch screen which responds to finger movements. In an example, the two displays can display two different sections of the same text content. In an example, the two displays can display two different sections of the same image content. In an example, the two displays can display text and image, respectively, from the same multi-media content. In an example, the two displays can have complementary shapes whose sides fit together which the device is in the second configuration. Other example variations discussed in this disclosure or in priority-linked disclosures can also be applied to this example where relevant.

Figure 8:
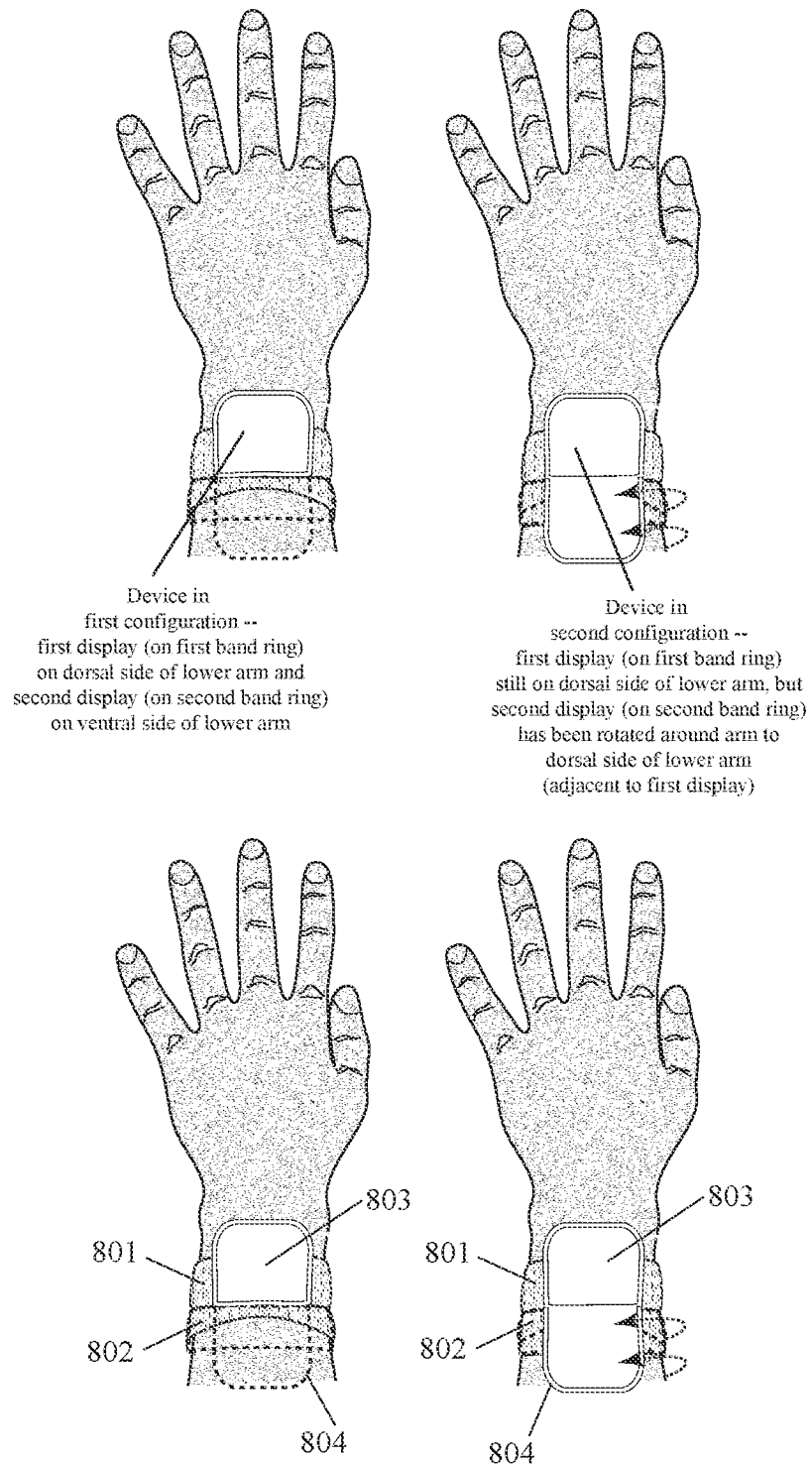
FIG. 8 shows a wrist-worn device with two bands which are rotated relative to each other to align two planoconvex displays.

FIG. 8 shows two sets of two sequential views of a wrist-worn computing device with a multi-configuration display. The upper set has conceptual labeling. The upper set provides conceptual insight into this example, with written explanations instead of component numbers. The lower set has specific component labeling. The lower set shows this same example in conventional patent diagram format with component numbers. These two different perspectives of the same example (in the upper and lower portions of FIG. 8, respectively) combine to provide the reader with a better conceptual understanding of the invention than either perspective alone.

FIG. 8 shows a wrist-worn computing device with a multi-configuration display comprising: a proximal band which is worn around a person's wrist and/or arm; a distal band which is worn around the person's wrist and/or arm;

wherein the proximal band and the distal band are attached to each other in a manner which allows one band to rotate relative to the other band; a first display on the proximal band; a second display on the distal band; wherein the device has a first configuration in which the first display and the second display are on different sides of the person's wrist and/or arm; wherein the device has a second configuration in which the first display and the second display are aligned on the same side of the person's wrist in order to form a (large) combined display; and wherein the device is changed from its first configuration to its second configuration by rotating one of the bands relative to the other band.

The lower half of FIG. 8 shows two sequential views of a wearable computing device for the wrist and/or arm comprising: a proximal band 802 which is worn around a person's wrist and/or arm; a distal band 801 which is worn around the person's wrist and/or arm; wherein the proximal band and the distal band are attached to each other in a manner which allows one band to rotate relative to the other band; a first display 804 on the proximal band; a second display 803 on the distal band; wherein the device has a first configuration in which the first display and the second display are on different sides of the person's wrist and/or arm; wherein the device has a second configuration in which the first display and the second display are aligned on the same side of the person's wrist in order to form a (large) combined display; and wherein the device is changed from its first configuration to its second configuration by rotating one of the bands relative to the other band.

In an example, the sides of the first and second displays which face toward each other in the second configuration can fit together in the second configuration to form a larger combined display. In an example, the first and second displays can combine to form a larger display with a rounded quadrilateral shape in the second configuration. In an example, the first and second displays can combine to form a larger display with a circular shape in the second configuration. In an example, the sides of the first and second displays which face toward each other in the second configuration can be straight. In an example, the sides of the first and second displays which face away from other in the second configuration can be arcuate. In an example, the first and second displays can snap, latch, and/or lock together in the second configuration to form a stable larger display, but also be subsequently unsnapped, unlatched, and/or unlocked by the wearer to return the device to the first configuration. Other example variations discussed in this disclosure or in priority-linked disclosures can also be applied to this example where relevant.

Figure 9:
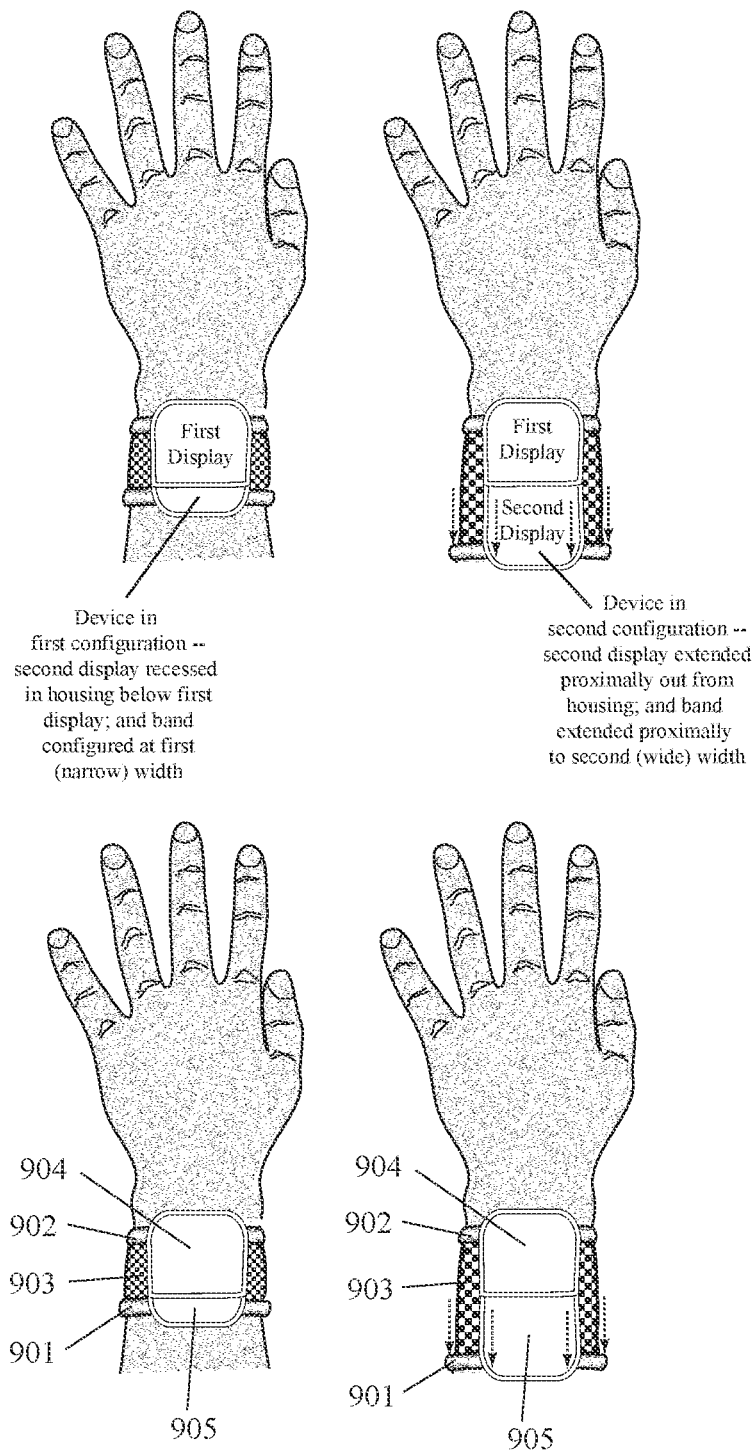
FIG. 9 shows a wrist-worn device with a sliding secondary display and an expandable mesh.

FIG. 9 shows two sequential views of a wrist-worn computing device with a multi-configuration display comprising: a band which is worn around a person's wrist and/or arm; wherein the band further comprises a proximal ring; wherein the band further comprises a distal ring; wherein the band further comprises an expandable mesh (or fabric) between the proximal ring and the distal ring; a first display which is attached to the distal ring; and a second display which is attached to the proximal ring, wherein one of the displays slides under (and out from under) the other display. The upper half of FIG. 9 provides conceptual insight into this example, with written explanations instead of component numbers. The lower half of FIG. 9 shows this same example in conventional patent diagram format with component numbers. These two different perspectives of the same example (in the upper and lower halves of FIG. 9, respectively) combine to provide the reader with a better conceptual understanding of the invention than either perspective alone.

The lower half of FIG. 9 shows two sequential views of a wearable computing device for the wrist and/or arm comprising: a band which is worn on a person's wrist and/or arm; wherein the band further comprises a proximal ring 901; wherein the band further comprises a distal ring 902; wherein the band further comprises an expandable mesh (or fabric) 903 between the proximal ring and the distal ring; a first display 904 which is attached to the distal ring; and a second display 905 which is attached to the proximal ring, wherein one of the displays slides under (and out from under) the other display. In an example, the expandable mesh (or fabric) can be between the displays and the surface of the person's wrist and/or arm. The expandable mesh (or fabric) can keep the device from pinching the person's skin as one or both of the rings and displays are moved relative to each other.

In an example, an expandable mesh (or fabric) between a proximal ring and a distal ring can unroll and/or uncoil out from inside the proximal ring or the distal ring as the two rings are moved apart from each other. In an example, an expandable mesh (or fabric) between a proximal ring and a distal ring can be elastic and can stretch as the two rings are moved apart from each other. In an example, one of the displays can slide out from the interior of the other display. In an example, the two displays can be telescoped relative to each other. In an example, one display can telescope out from the other display.

In an example, a display can be a computer screen. In an example, a display can have a cross-sectional shape which is selected from the group consisting of: rectangular with rounded vertexes, hexagonal with rounded vertexes, square, rectangular, hexagonal, circular, elliptical, and oblong. In an example, the two displays can be centrally aligned along the same proximal-to-distal axis of the person's wrist and/or forearm. In an example, a display can have a flat display surface. In an example, a display can be a touch screen which responds to finger movements. In an example, the two displays can display two different sections of the same text content. In an example, the two displays can display two different sections of the same image content. In an example, the two displays can display text and image, respectively, from the same multi-media content. In an example, the two displays can have complementary shapes whose sides fit together which the rings are moved apart from each other. Other example variations discussed in this disclosure or in priority-linked disclosures can also be applied to this example where relevant.

Figure 10:
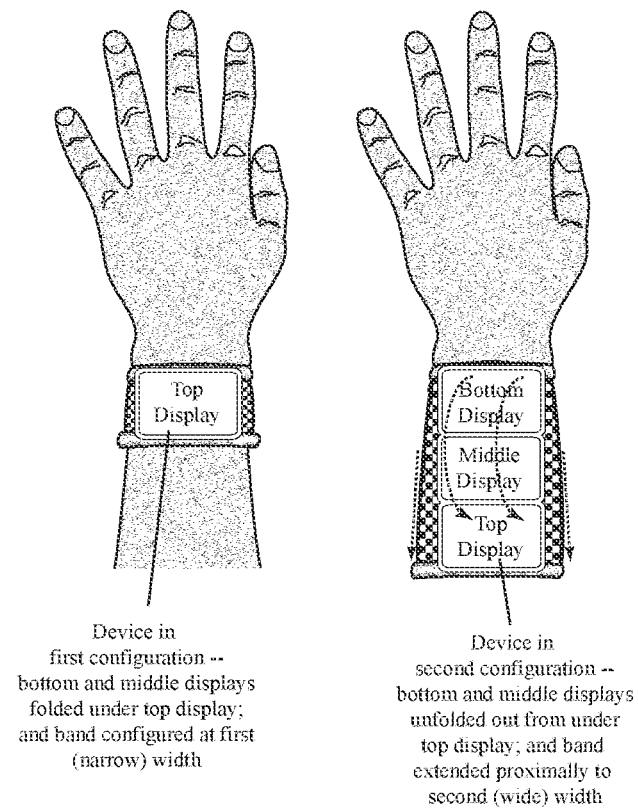
FIG. 10 shows a wrist-worn device with unfolding displays and a variable-width band.
Figure 10:
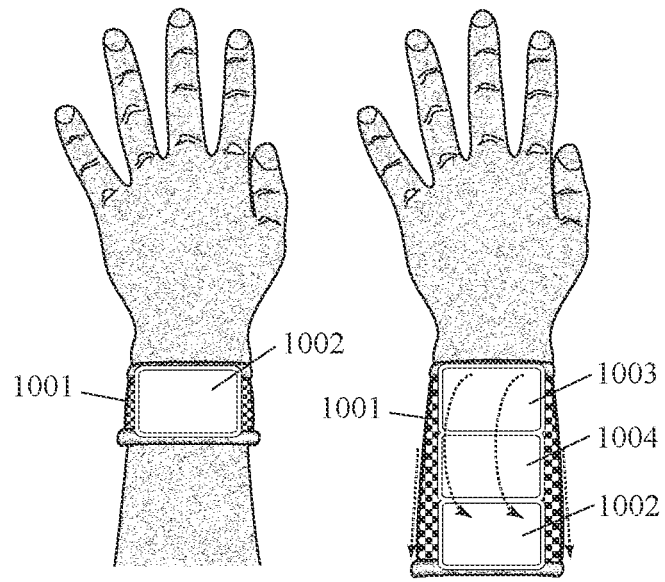

FIG. 10 shows two sequential views of a wrist-worn computing device with a multi-configuration display comprising: a variable-width band which is worn around a person's wrist and/or arm; a plurality of displays (three in this case) which are attached to the variable-width band; wherein the device has a first configuration in which displays in the plurality of displays overlap each other by a first amount and the variable-width band has a first width; wherein the device has a second configuration in which displays in the plurality of displays overlap each other by a second amount and the variable-width band has a second width, wherein the second amount is less than the first amount, and wherein the second width is greater than the first width; wherein the device is changed from the first configuration to the second configuration by unfolding one or more displays in a proximal direction relative to the other displays and by expanding and/or stretching the width of the band in a proximal direction. The upper half of FIG. 10 provides conceptual insight into this example, with written explanations instead of component numbers. The lower half of FIG. 10 shows this same example in conventional patent diagram format with component numbers. These two different perspectives of the same example (in the upper and lower halves of FIG. 10, respectively) combine to provide the reader with a better conceptual understanding of the invention than either perspective alone.

The lower half of FIG. 10 shows two sequential views of a wearable computing device for the wrist and/or arm comprising: a variable-width band 1001 which is worn around a person's wrist and/or arm; a plurality of displays (three in this case) 1002, 1003, and 1004, which are attached to the variable-width band; wherein the device has a first configuration in which displays in the plurality of displays overlap each other by a first amount and the variable-width band has a first width; wherein the device has a second configuration in which displays in the plurality of displays overlap each other by a second amount and the variable-width band has a second width, wherein the second amount is less than the first amount, and wherein the second width is greater than the first width; wherein the device is changed from the first configuration to the second configuration by unfolding (or "flipping") one or more displays in a proximal direction relative to the other displays and by expanding and/or stretching the width of the band in a proximal direction. In an example, the variable-width band can unroll and/or uncoil. In an example, the variable-width band can be elastic and can stretch. Other example variations discussed in this disclosure or in priority-linked disclosures can also be applied to this example where relevant.

Figure 11:
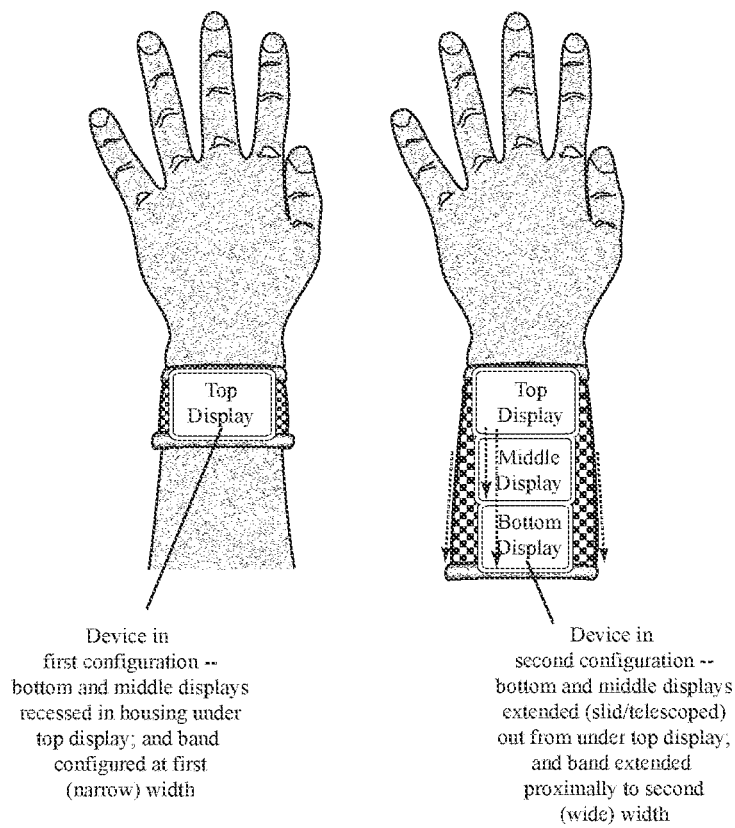
FIG. 11 shows a wrist-worn device with telescoping displays and a variable-width band.
Figure 11:
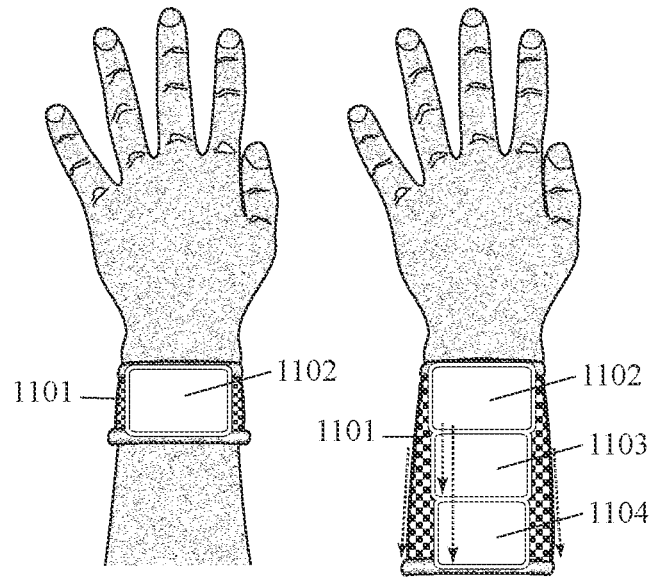

FIG. 11 shows two sequential views of a wrist-worn computing device with a multi-configuration display comprising: a variable-width band which is worn around a person's wrist and/or arm; a telescoping series of displays which are attached to the variable-width band; wherein the device has a first configuration in which displays in the telescoping series of displays are inside each other to a first extent and the variable-width band has a first width; wherein the device has a second configuration in which displays in the telescoping series of displays are inside each other to a second extent and the variable-width band has a second width, wherein the second extent is less than the first extent, and wherein the second width is greater than the first width; wherein the device is changed from the first configuration to the second configuration by un-telescoping (e.g. sliding out) displays in a proximal direction and by expanding and/or stretching the width of the band in a proximal direction. The upper half of FIG. 11 provides conceptual insight into this example, with written explanations instead of component numbers. The lower half of FIG. 11 shows this same example in conventional patent diagram format with component numbers. These two different perspectives of the same example (in the upper and lower halves of FIG. 11, respectively) combine to provide the reader with a better conceptual understanding of the invention than either perspective alone.

The lower half of FIG. 11 shows two sequential views of a wearable computing device for the wrist and/or arm comprising: a variable-width band 1101 which is worn around a person's wrist and/or arm; a telescoping series of displays, 1102, 1103, and 1104, which are attached to the variable-width band; wherein the device has a first configuration in which displays in the telescoping series of displays are inside each other to a first extent and the variable-width band has a first width; wherein the device has a second configuration in which displays in the telescoping series of displays are inside each other to a second extent and the variable-width band has a second width, wherein the second extent is less than the first extent, and wherein the second width is greater than the first width; wherein the device is changed from the first configuration to the second configuration by un-telescoping (e.g. sliding out) displays in a proximal direction and by expanding and/or stretching the width of the band in a proximal direction. In an example, the variable-width band can unroll and/or uncoil. In an example, the variable-width band can be elastic and can stretch. Other example variations discussed in this disclosure or in priority-linked disclosures can also be applied to this example where relevant.

Figure 12:
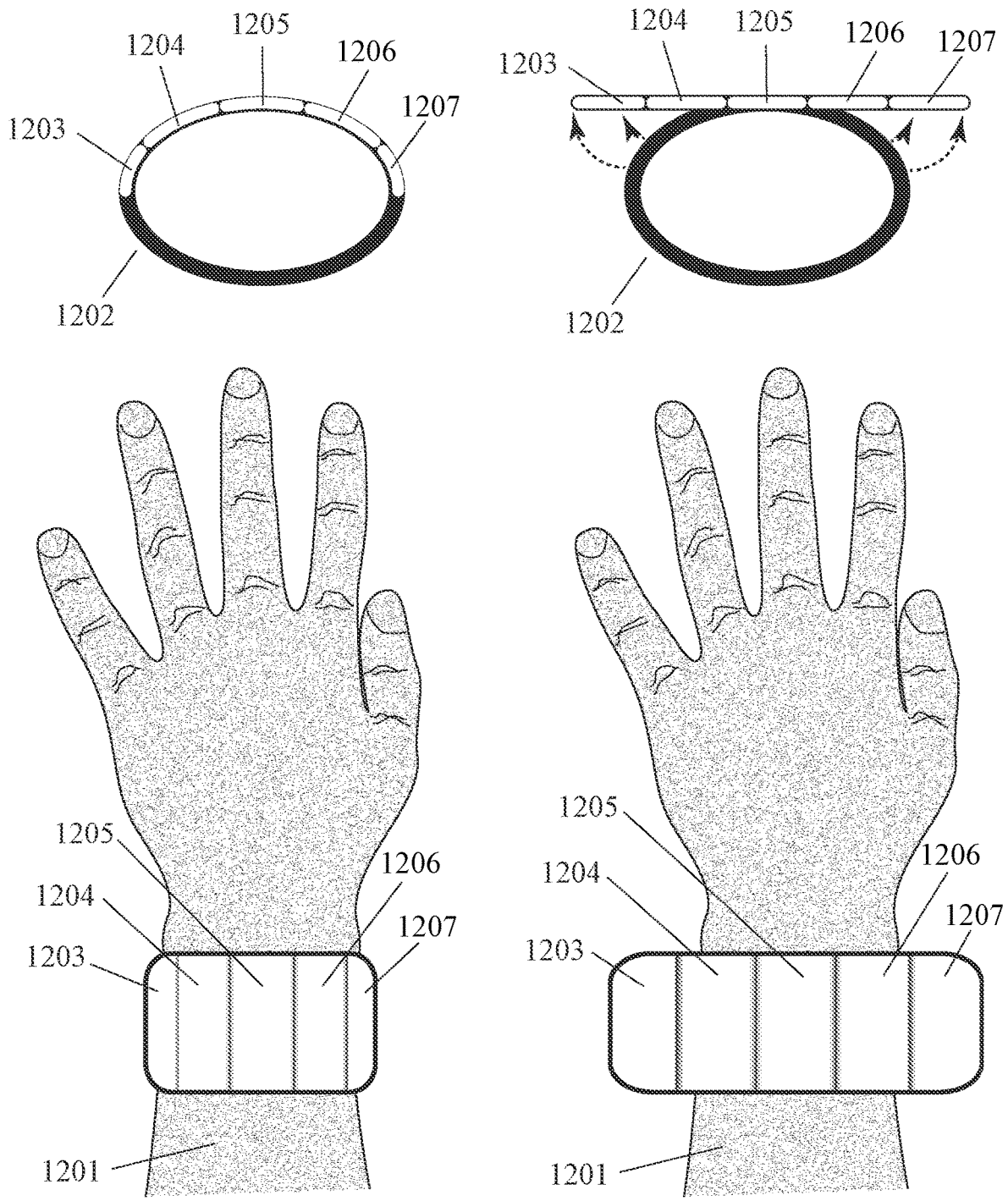
FIG. 12 shows a wrist-worn device with an array of displays having a non-coplanar first configuration and a coplanar second configuration.

FIG. 12 shows four views, from two different perspectives and at two different times, of an example of a wearable computing device for the wrist and/or arm. The upper left portion of FIG. 12 shows a side (proximal to distal) view of this device at a first point in time (before a plurality of displays of the device are aligned and coplanar) and the lower left portion of FIG. 12 shows a top-down view of this device on a person's wrist at this first point in time. The upper right portion of FIG. 12 shows a side (proximal to distal) view of this device at a second point in time (after the plurality of displays of the device have been aligned and made coplanar) and the lower right portion of FIG. 12 shows a top-down view of this device on a person's wrist at this second point in time. Proximal means closer to a person's elbow and distal means closer to the person's fingers.

This example of a wearable computing device for the wrist and/or arm comprises: a band (e.g. band, strap, or bracelet) which is attached to (e.g. encircles) a person's wrist and/or arm; and a plurality of displays which collectively span at least 40% of the circumference of the band; wherein the device has a first configuration in which the displays are not coplanar (e.g. in the same virtual plane) and a second configuration in which the displays are coplanar. This allows the person to view (and touch) a larger surface area of combined displays in the second configuration without having to rotate and contort their wrist and/or arm. This device also enables a person to have a large, flat display on their wrist and/or arm (in the second configuration) when needed, but not have the device stick out when the larger, flat screen is not needed. If the device were to stick out all the time, then it could get caught on external objects or restrict movement of the person's wrist and/or arm.

With respect to specific components, FIG. 12 shows an example of a wearable computing device for the wrist and/or arm comprising: an attachment member 1202 (e.g. a band, strap, or bracelet) which is configured to be attached to (e.g. encircle) a person's wrist and/or arm 1201; and a plurality of displays (including displays 1203, 1204, 1205, 1206, and 1207) which collectively span at least 40% of the circumference of the attachment member; wherein the device has a first configuration in which the plurality of displays are not coplanar (e.g. not in the same virtual plane) and a second configuration in which the plurality of displays are coplanar.

In an example, the plurality of displays can collectively curve around at least 40% of the circumference of the attachment member when the device is in the first configuration. In an example, the plurality of displays can collectively curve around between 40% and 75% of the circumference of the attachment member when the device is in the first configuration. In an example, displays in the plurality of displays can be arcuate in their first configuration. In an example, in the first configuration a plurality of displays can collectively span between 40% and 60% of the circumference of an attachment member. In an example, in the first configuration a plurality of displays can collectively span between 40% and 80% of the circumference of an attachment member. In an example, in the first configuration a plurality of displays can collectively span between 60% and 100% of the circumference of an attachment member.

In an example, in the first configuration, a plurality of displays can collectively have a side-view shape which is a section of a circle, ellipse, or oval. In an example, in the first configuration, the plurality of displays collectively have a side-view shape which is a section of a hexagon, octagon, decagon, or other equilateral polygon, but in the second configuration the plurality of displays have a side-view shape which is a straight line. In an example, in the first configuration the plurality of displays are collectively flat, but in the second configuration the plurality of displays are curved. In an example, the plurality of displays can be flat in the second configuration. In an example, the plurality of displays can be coplanar in the second configuration. In an example, the plurality of displays can be coplanar in a plane which is tangential to the circumference of the attachment member in the second configuration.

In an example, a plurality of displays in the first configuration can combine to have a shape which, when viewed from a side (proximal to distal) perspective, is a circle, an arc of a circle, and/or conic section. In an example, a plurality of displays in the first configuration can combine to have a shape which, when viewed from a side (proximal to distal) perspective, is a polygon or a spline segment of a polygon. In an example, a plurality of displays in the second configuration can combine to have a shape which is a flat plane.

In an example, the plurality of displays can be a sequence or series of individual screens spanning at least 40% of the circumference of the attachment member, wherein the individual screens are connected to each other by flexible joints, hinges, links, or fabric connections. In an example, the plurality of displays can be a sequence or series of individual flat screens spanning at least 40% of the circumference of the attachment member, wherein the individual screens are connected to each other by flexible joints, hinges, links, or fabric connections. In an example, the plurality of displays can be a sequence or series of individual curved screens spanning at least 40% of the circumference of the attachment member, wherein the individual screens are connected to each other by flexible joints, hinges, links, or fabric connections. In an example, this device can be made with a single bendable display instead of a plurality of individual displays. In an example, a single bendable display can curve around at least 40% of the circumference of an attachment member in a first configuration and can be flat (and tangential to the attachment member) in a second configuration.

In an example, gaps (non-display portions) between displays in a plurality of displays can comprise no more than 10% of the portion of the circumference of the attachment member which the displays collectively span. In an example, gaps (non-display portions) between displays in a plurality of displays can comprise no more than 20% of the portion of the circumference of the attachment member which the displays collectively span. In an example, displays in the plurality of displays can be flat in their first configuration. In an example, a plurality of displays can intersect (or at least their virtual planes can intersect) at angles within the range of 30 to 60 degrees in the first configuration.

In an example, displays in the plurality of displays are a first maximum distance from the attachment member in the first configuration and are a second maximum distance from the attachment member in the second configuration, wherein the second maximum distance is at least 50% greater than the first maximum distance. In an example, the device has a first width in a top-down view in the first configuration and has a second width in the top-down view in the second configuration, wherein the second width is at least 25% greater than the first width.

In an example, displays in the plurality of displays can be connected to each other by flexible joints, hinges, links, or fabric connections. In an example, joints, hinges, axles, or links which connect displays can have reversible locking mechanisms (e.g. locking, snapping, spring, latch, or tensile mechanisms) which reversibly lock the displays into their first configuration and/or into their second configuration. This enables the person to (temporarily) lock the plurality of displays into their coplanar second configuration for use as a larger flat display and touch screen and then lock them back into their circumferential first configuration when not in use as a larger flat display and touch screen. In an example, the displays can snap or latch into their respective places around the circumference of the attachment member in their first configuration and lock into their respective places in a plane in their second configuration.

In an example, the plurality of displays can comprise three displays. In an example, the plurality of displays can comprise three displays. In an example, the plurality of displays can comprise six displays. In an example, the plurality of displays can comprise eight displays. In an example, displays in the plurality of displays can all be the same size. In an example, a display in the center of the dorsal surface of the person's wrist and/or arm can be larger than other displays in the plurality of displays.

In an example, individual displays in the plurality of displays can be longitudinal with longitudinal axes which are perpendicular to the plane of the circumference of the band, but collectively they can form a large combined display (in the second configuration) with a longitudinal axis which is parallel to the plane of the circumference of the band. In another example, not shown in FIG. 12, the device can also have a third configuration, wherein the longitudinal axis of the large combined display (comprising the plurality of displays) is rotated to an orientation which is perpendicular to the plane of the circumference of the band. In this latter case, the plurality of displays have a first configuration in which they collectively curve around a portion of the circumference of the band, have a second configuration in which they are coplanar with a longitudinal axis which is parallel to the circumference of the band, and have a third configuration in which they are coplanar with a longitudinal axis which is perpendicular to the circumference of the band.

In an example, different displays can show different images and/or serve different interface functions. In an example, one display can show an image of the wearer and the other display can show an image of a person with whom the wearer is communicating. In an example one display can show an image and the other display can show text or a control pad. In an example, the one display can display a summary of the information which is displayed in more detail on other displays. In another example, two or more displays can show two portions of the same image. In an example, two or more displays can combine to function as a single larger display in the second configuration. Other example variations discussed in this disclosure or in priority-linked disclosures can also be applied to this example where relevant.

Figure 13:
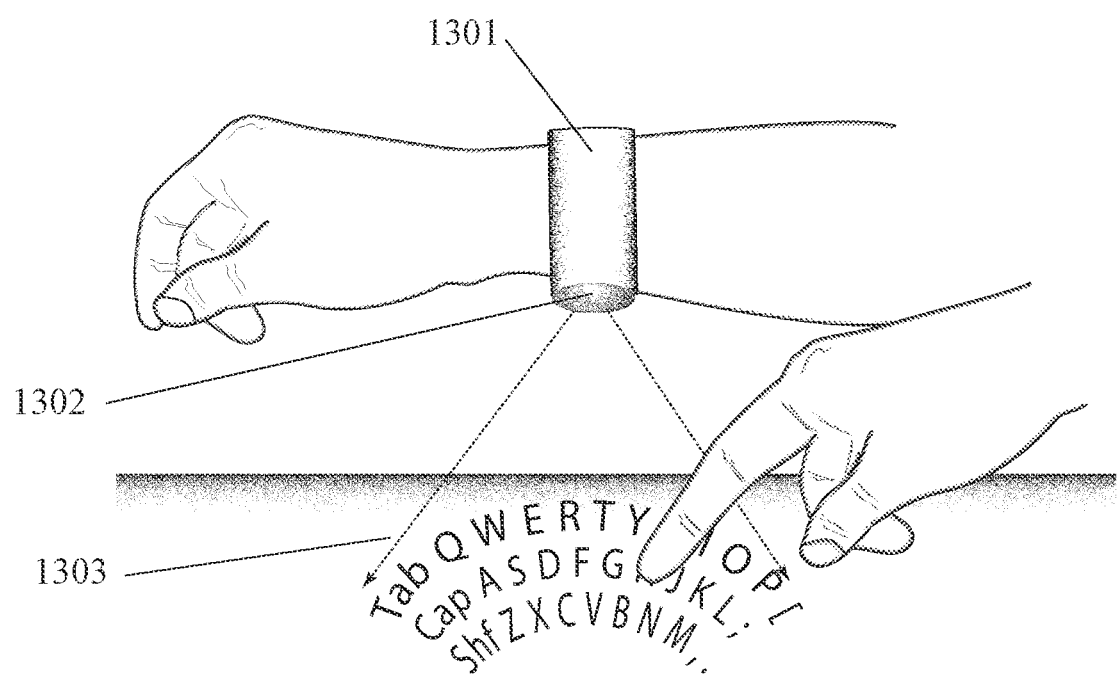
FIG. 13 shows a wrist-worn device which projects a virtual image and detects finger movement on this virtual image.

FIG. 13 shows an example of a wearable computing device for the wrist and/or arm comprising: an attachment member 1301, (e.g. a band, strap, bracelet, or sleeve) which is worn on (e.g. encircles) a person's wrist and/or arm; and an image projector 1302 on the attachment member which projects a virtual image (e.g. a virtual keyboard and/or virtual array of icons) 1303 onto a nearby surface, wherein hand and/or finger gestures relative to the projected virtual image are detected. In an example, this device can project a virtual user interface and detect virtual contact between the wearer and this virtual interface. This device can serve as a human-to-computer user interface.

In an example, the image projector can be located on the ventral side of the attachment member. In an example, the image projector can project an image with coherent light. In an example, the image projector can be a laser image projector. In an example, the device can further comprise a display (e.g. a touch screen) on the dorsal side of the attachment member. In an example, the device can further comprise a display (e.g. a touch screen) on a lateral (e.g. right or left) side of the attachment member. In an example, this device can further comprise a camera which records hand and/or finger gestures relative to the projected virtual image. In an example, the camera can be located on the ventral side of the attachment member.

In an example, the focal direction of a virtual image projected out from a device can be along a radial line which extends out from the center of the circumference of the device. In an example, the central focal vector of a virtual image projected out from a device can be substantially parallel with the plane of the circumference of the device. In an example, the central focal vector of a virtual image projected out from a device can be automatically adjusted based on the orientation and/or angle of a nearby surface relative to the device. In an example, the central focal vector of a virtual image projected out from a device can be automatically adjusted based on movement of the device relative to a nearby surface. In an example, the focal distance of a virtual image projected out from a device can be automatically adjusted based on movement of the device relative to a nearby surface.

In an example, a device can further comprise a data processor which analyzes images recorded by the camera to identify hand and/or finger gestures and/or positions relative to the projected virtual image. In an example, the data processor can have pattern recognition software. In an example, the device can further comprise an infrared light emitter and reflection detector. In an example, an infrared light emitter and reflection detector can be used to detect the location of a person's finger relative to projected virtual image.

In an example, a device can further comprise one or more sensors selected from the group consisting of: accelerometer, blood pressure sensor, camera or other imaging sensor, electrochemical sensor, electrogoniometer, electromyography (EMG) sensor or other electromagnetic sensor, optoelectronic sensor, galvanic skin response (GSR) sensor, glucose sensor, gyroscope, heart rate sensor, inclinometer, infrared light sensor, ultraviolet light sensor, microphone or other sound sensor, neurosensor, motion sensor, piezoelectric sensor, pressure sensor, blood oximetry sensor, spectroscopic sensor or other light-spectrum-analyzing sensor, strain gauge, ultrasonic sensor, MEMS sensor, GPS sensor, compass, magnetometer, humidity sensor, food consumption detector, and temperature sensor.

In an example, a device can communicate with a handheld electronic device, a different wearable technology device, an array of wearable sensors, a communication network tower, a satellite, a home control system, and/or an implantable medical device. In an example, a device can further comprise one or more components selected from the group consisting of: data processing member; data transmitting member; data receiving member; power source; energy harvester; one or more LEDs; one or more sound-emitting members; one or more tactile-sensation-creating members; one or more neurostimulators, myostimulators, or other electromagnetic energy emitters; one or more hardware buttons, knobs, or keys; speech-recognition interface, and eye-gaze-tracking interface. Other example variations discussed in this disclosure or in priority-linked disclosures can also be applied to this example where relevant.

Figure 14:
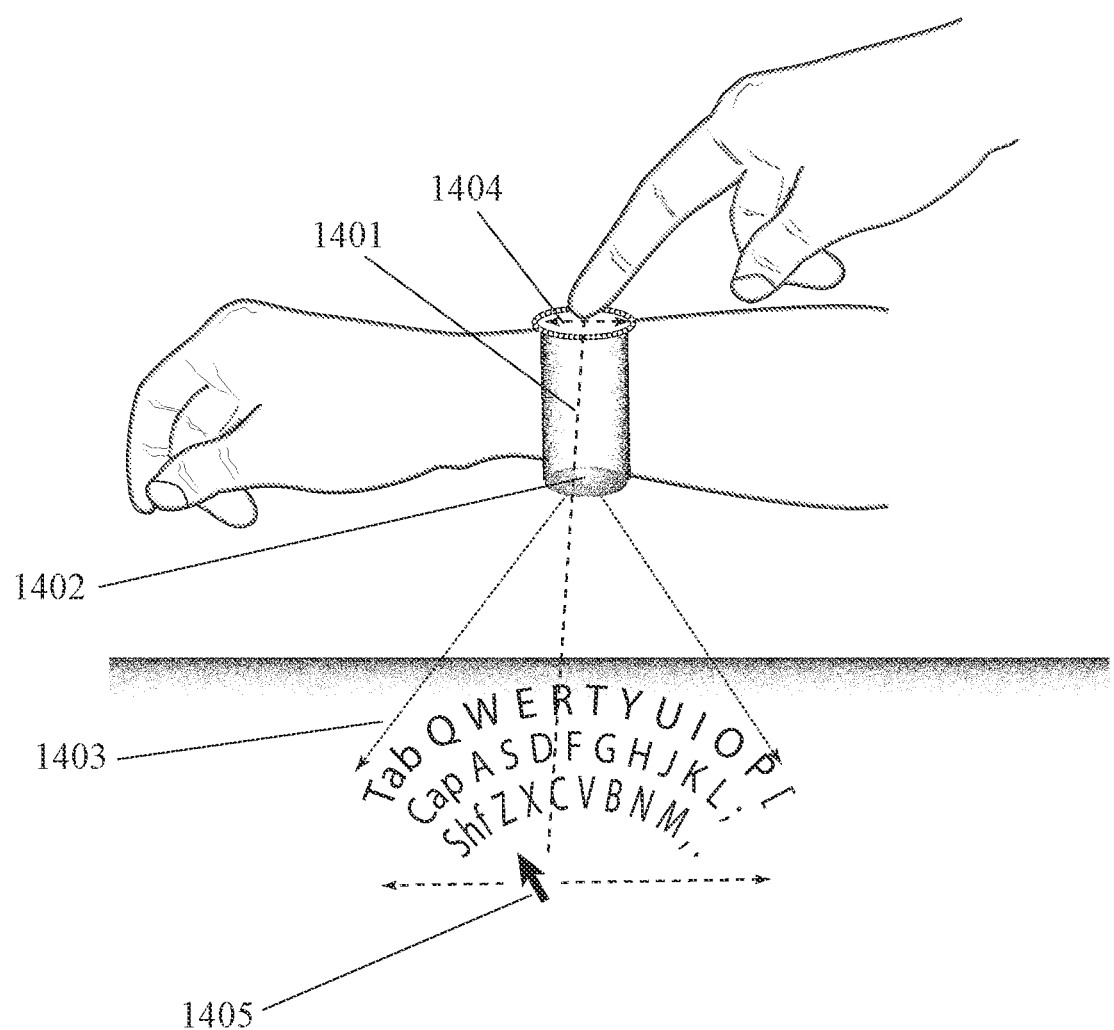
FIG. 14 shows a wrist-worn device which projects a virtual image and detects finger movement on touch screen.

FIG. 14 shows an example of a wearable computing device for the wrist and/or arm which is similar to the one shown in FIG. 13 except that movement of a person's finger on a touch screen moves a cursor in a projected virtual image instead of image-based detection of a person's finger moving over the actual projected image. One advantage of this design as compared to the design shown in FIG. 13 is that a portion of the projected virtual image is not obscured by the person's finger.

FIG. 14 shows an example of a wearable computing device for the wrist and/or arm comprising: an attachment member 1401, such as a band or strap, which is worn on a person's wrist and/or arm; an image projector 1402 on the attachment member which projects a virtual image (e.g. a keyboard) 1403 onto a nearby surface; and a touch screen 1404 on the attachment member which controls a cursor 1405 in the virtual image, wherein the cursor is displayed as part of the virtual image. In an example, the person can move the cursor to different locations on the virtual image by moving their finger relative to the touch screen. In an example, this device can serve as a human-to-computer user interface. In an example, the image projector can be located on the ventral side of the person's wrist and/or arm. In an example, the touch screen can be located on the dorsal side of the person's wrist and/or arm. Other example variations discussed in this disclosure or in priority-linked disclosures can also be applied to this example where relevant.

Figure 15:
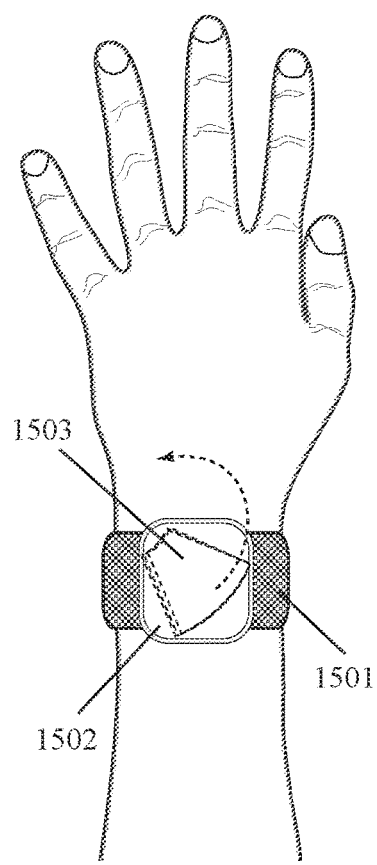
FIGS. 15 through 17 show a wrist-worn device with a plurality of secondary displays which fan out from a primary display.
Figure 16:
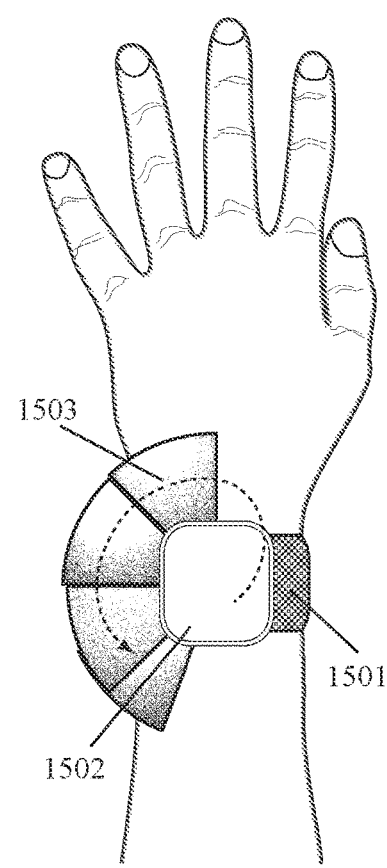
Figure 17:
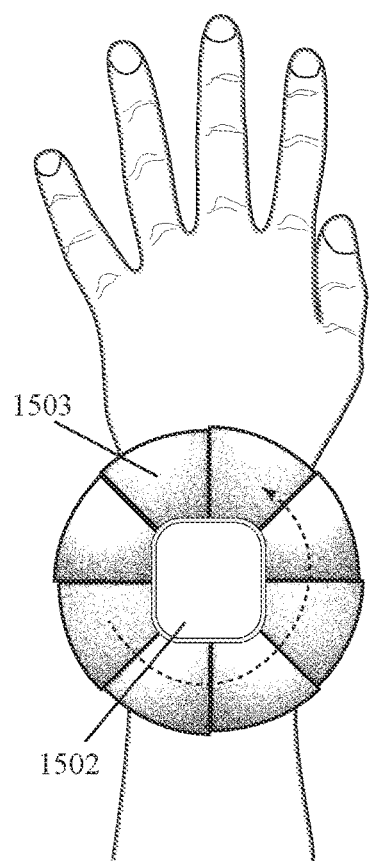

FIGS. 15 through 17 show a wearable computing device comprising: a band which is worn around a person's wrist and/or arm; a primary display on the band; and a plurality of secondary displays underneath the primary display (or a housing to which the primary display is attached) in a first configuration and extending out from the primary display (or a housing to which the primary display is attached) to form a larger combined display area in a second configuration. In this example, in the second configuration, the secondary displays fan out from the primary display (or a housing to which the primary display is attached) to form a circular combined display area. This design enables the device to expand (in the second configuration) to a large display area when needed, but be compact and unobtrusive (in the first configuration) when a large display area is not needed.

With respect to specific components, FIGS. 15 through 17 show three views, at three different times, of an example of a wearable computing device for the wrist and/or arm comprising: an attachment member (e.g. a strap or band) 1501 which is attached to a person's wrist and/or arm; a primary display 1502 on the attachment member; and a plurality of secondary displays 1503, wherein the device has a first configuration in which the plurality of secondary displays are under the primary display and overlap each other to a first extent; wherein the device has a second configuration in which the plurality of secondary displays extend out from the primary display and overlap each other to a second extent; and wherein the second extent is less than the first extent.

In an example, secondary displays can be moved manually from their first configuration to their second configuration. In an example, the secondary displays can be moved manually by the person wearing the device. In an example, secondary displays can be compelled to move from their first configuration to their second configuration by a spring, elastic band, or other tensile element when a snap, latch, or other locking mechanism is released by the person. The secondary displays can also be unsnapped, unlatched, or unlocked and moved back under the primary display (or housing) when the larger composite display is not needed. Alternatively, secondary displays can be moved automatically from their first configuration to their second configuration by an actuator in the device. In an example, the device can comprise a housing to which the primary display is attached. In an example, secondary displays can be inside this housing in the first configuration and can pivot, rotate, and/or slide out from this housing in the second configuration.

In an example, secondary displays can combine to form a large composite display in their second configuration. In an example, this large composite display can have a circular, semicircular, or quadrilateral shape. In an example, secondary displays can "fan out" as they extend out from a primary display or housing. In an example, secondary displays can each have the same shape and size. In an example, this shape can be selected from the group consisting of: pie slice, keystone shaped, wedge shape, trapezoid, fan shape, and flower petal shape. In an example, different secondary displays can have different shapes and/or sizes. In an example, there can be eight secondary displays. In an example, there can be four or six secondary displays. As shown in FIGS. 15 through 17, a composite display which is composed of the primary and secondary displays in the second configuration can look like a "flower with petals", wherein the primary display is like the center of the flower and the secondary displays are like petals of the flower.

In an example, there can be a housing on an attachment member on which a primary display is located. In an example, secondary displays can be inside this housing in their first configuration. In an example, secondary displays can pivot, rotate, and/or slide out from the interior of the housing as the device transitions from its first configuration to its second configuration. As shown in FIGS. 15 through 17, secondary displays can overlap when they are first collectively extended out from the housing, but then their degree of overlap decreases as they fan out radially (in a circle) around the primary display. In an alternative example, each secondary display can be extended out individually from different locations (e.g. from different sides) of the housing. In an example, the number of secondary displays can be the same as the number of sides on a polygonal primary display (or housing).

In an example, a wearable computing device for the wrist and/or arm can comprise: a band which is attached to a person's wrist and/or arm; a housing on the dorsal side of the band; a primary display on the housing; and a plurality of secondary displays, wherein the secondary displays have a first configuration in which they are inside the housing, and wherein the secondary displays have a second configuration in which they pivot, rotate, and/or slide out from the housing and combine to form a composite display. In an example, a wearable computing device for the wrist and/or arm can comprise: a band which is attached to a person's wrist and/or arm; a housing on the dorsal side of the band; a primary display on the housing; and a plurality of pie, keystone, or wedge shaped secondary displays, wherein the secondary displays have a first configuration in which they are in the housing, and wherein the secondary displays have a second configuration in which they pivot, rotate, and/or slide out from the housing and combine to form a circular composite display.

In an example, a wearable computing device for the wrist and/or arm can comprise: a strap or band which is attached to a person's wrist and/or arm; a housing on the dorsal side of the strap or band; a primary display on the housing; and a plurality of secondary displays, wherein the secondary displays have a first configuration in which they are in the housing, and wherein the secondary displays have a second configuration in which they slide, pivot, or rotate out from the housing and combine with the primary display to form a large circular display. In an example, a wearable computing device for the wrist and/or arm can comprise: a strap or band which is attached to a person's wrist and/or arm; a housing on the dorsal side of the strap or band; a primary display on the housing; and a plurality of secondary displays, wherein the secondary displays have a first configuration in which they are in the housing, and wherein the secondary displays have a second configuration in which they slide, pivot, or rotate out from the housing and combine with the primary display to form a large quadrilateral display. Other example variations discussed in this disclosure or in priority-linked disclosures can also be applied to this example where relevant.

Figure 18:
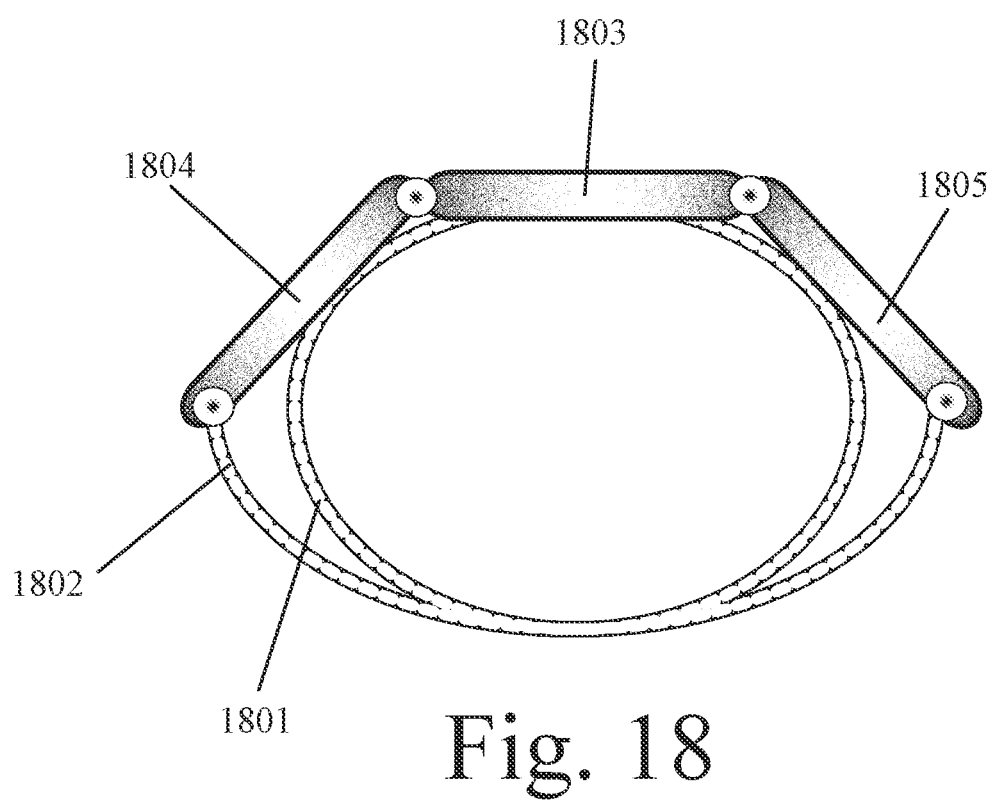
FIGS. 18 and 19 show a wrist-worn device with an inner band, an outer band, and an array of displays having a non-coplanar first configuration and a coplanar second configuration.
Figure 19:
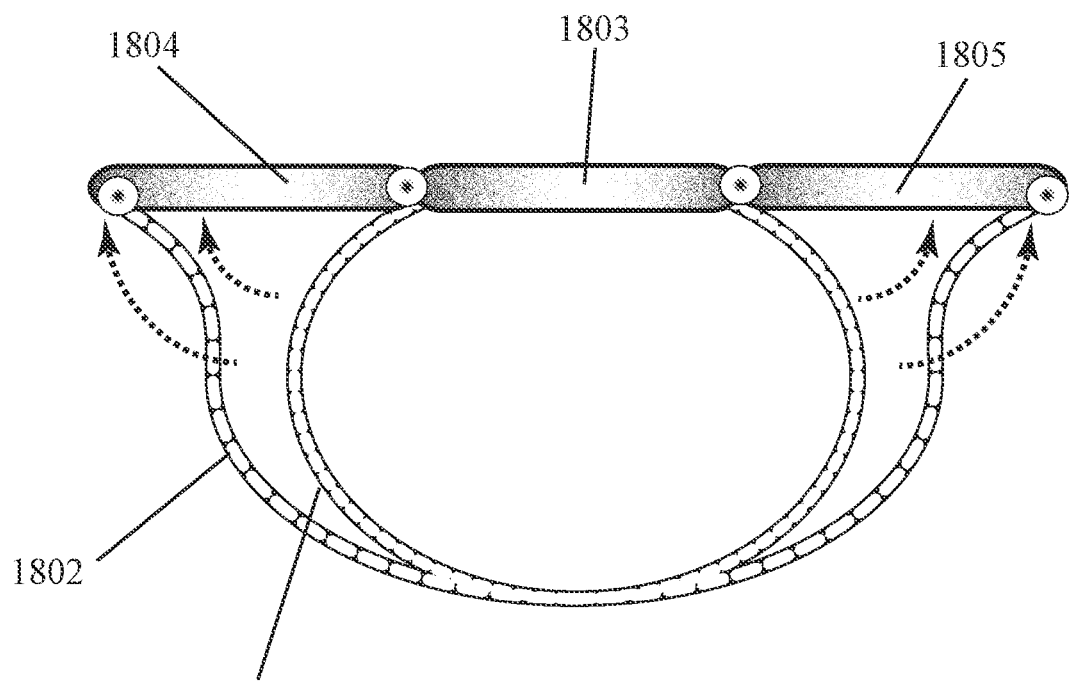

FIGS. 18 and 19 show (proximal-to-distal or elbow-to-finger) side views at two different times of a wearable computing device for the wrist and/or arm comprising: an inner band which worn around a person's wrist and/or arm; an outer band attached to the inner band; a primary display on the dorsal side of the device; a first secondary display on a first side of the primary display, wherein the first secondary display is attached to the outer band; a second secondary display on a second side of the primary display, wherein the second secondary display is attached to the outer band; wherein the device has a first configuration in which the primary display, the first secondary display, and the second secondary display are not coplanar; and wherein the device has a second configuration in which the primary display, the first secondary display, and the second secondary display are coplanar. The outer band or strap helps to prevent the secondary displays from being snagged on something (and breaking) when the device is in its second configuration.

With respect to specific components, FIGS. 18 and 19 show two side views, at two different times, of an example of a wearable computing device for the wrist and/or arm comprising: an inner band or strap 1801 which is attached to a person's wrist and/or arm; an outer band or strap 1802 which is attached to the inner band or strap, wherein the outer band or strap is farther from the person's wrist or arm than the inner band or strap; a primary display 1803 on the dorsal side of the device; a first secondary display 1804 on a first side of the primary display, wherein the first secondary display is attached to the outer band or strap; a second secondary display 1805 on a second side of the primary display, wherein the second secondary display is attached to the outer band or strap, and wherein the second side is opposite the first side; wherein the device has a first configuration in which the primary display, the first secondary display, and the second secondary display are not coplanar and wherein the outer band or strap is a first average distance from the inner band or strap; wherein the device has a second configuration in which the primary display, the first secondary display, and the second secondary display are coplanar and the wherein the outer band or strap is a second average distance from the inner band or strap; and wherein the second distance is greater than the first distance.

In an example, the inner band (or strap) can encircle the entire circumference of the person's wrist and/or arm, but the outer band (or strap) does not. In an example, the inner band (or strap) can encircle the entire circumference of the person's wrist and/or arm, but the outer band (or strap) only spans between 40% and 60% of this circumference. In an example, the inner band (or strap) can encircle the entire circumference of the person's wrist and/or arm, but the outer band (or strap) only spans half of this circumference. In an example, ends of the outer band (or strap) can be connected to edges of the secondary displays. In an example, instead of a single continuous outer band (or strap), there can be two outer bands (or straps), one on each side of the inner band. In an example, the inner band can be uniformly convex when the device is in either the first configuration or the second configuration, but the outer band can be partially convex and partially concave when the device is in the second configuration.

In an example, the primary display can be attached to the inner band (or strap). In an example, the primary display can be attached to the outer band (or strap). In an example, the primary display can be attached to a housing which is attached to the inner and/or the outer bands (or straps). In an example, a first side (or edge) of a secondary display can be attached to the primary display (or a housing to which the primary display is attached) and a second side (or edge) of the secondary display can be attached to the outer band (or strap).

In an example, primary and secondary displays can all be flat. In an example, a flat primary display and a flat secondary display can be in virtual planes which intersect at 45 degree angle in the first configuration. In an example, a flat primary display and a flat secondary display can be in virtual planes which intersect at an angle between 30 and 60 degrees in the first configuration. In an alternative example, a primary display and/or a secondary display can be arcuate and/or flexible. In an example, secondary displays can be moveably connected to a primary display (or a housing to which the primary display is attached) by joints, hinges, axles, or folds. In an example, secondary displays can be moveably connected to a primary display (or a housing to which the primary display is attached) by joints, hinges, axles, or folds which pivot or rotate. In an example, an outer band can be elastic and stretchable. In an example, an outer band can have an expandable chain-link structure.

In an example, the device can be moved from its first configuration to its second configuration by pivoting or rotating secondary displays upward into the same virtual plane as the virtual plane of the primary display. In an example, the secondary displays can be locked, latched, or snapped into place in their second configuration, but can also be subsequently unlocked, unlatched, and/or unsnapped back into their first configuration. In an example, there can be one primary display and two secondary displays, one secondary display on either side of the primary display. In an example, there can be one primary display and four secondary displays, two secondary displays on either side of the primary display. In an example, the primary display and secondary displays can collectively span between 30% and 55% of the circumference of the person's wrist and/or arm when the device is in the first configuration. In an example, the primary display and secondary displays can collectively span between 50% and 80% of the person's wrist and/or arm when the device is in the first configuration. Other example variations discussed in this disclosure or in priority-linked disclosures can also be applied to this example where relevant.

Figure 20:
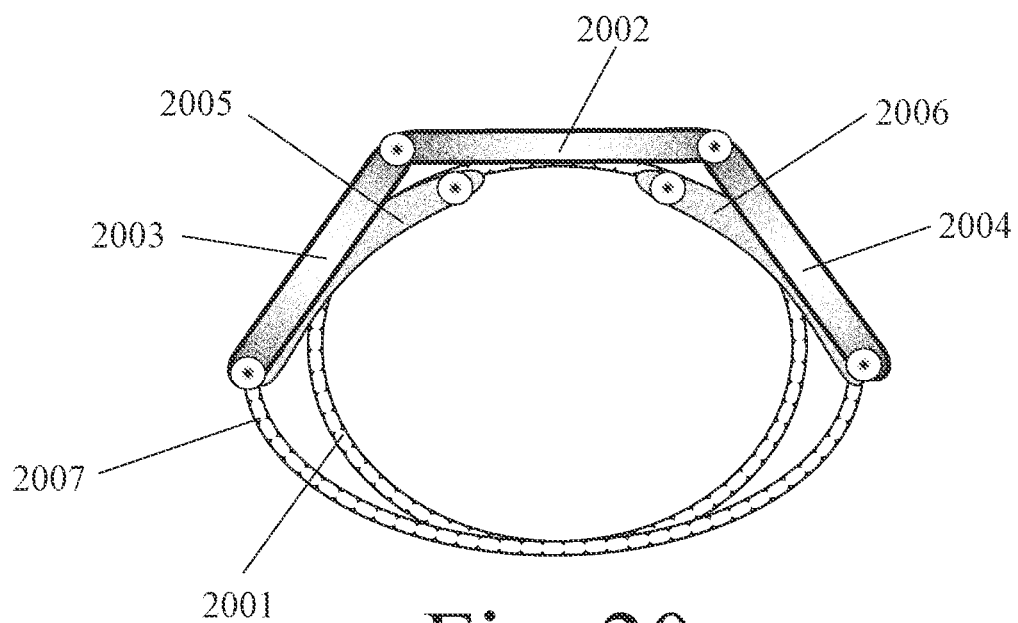
FIGS. 20 and 21 show a first example of a wrist-worn device with an inner band, a primary display, and secondary displays which are attached to folding arcuate segments.
Figure 21:
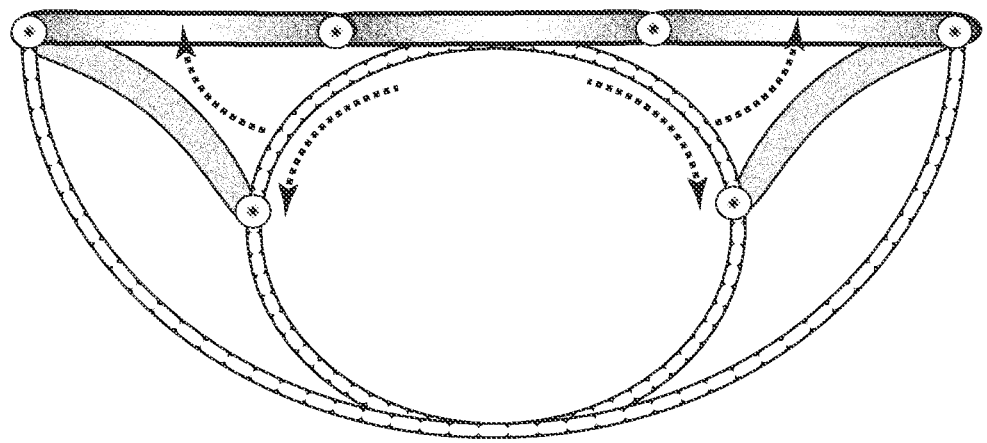

FIGS. 20 and 21 show side views at two different times of a wearable computing device for the wrist and/or arm comprising: a band worn around a person's wrist and/or arm; a primary display on the dorsal side of the band; a first secondary display on one side of the primary display; a first arcuate segment which connects the first secondary display to the band; a second secondary display on the other side of the primary display; and a second arcuate segment which connects the second secondary display to the band; wherein the device has a first configuration in which the arcuate segments are folded in toward the band and the displays are not coplanar; and wherein the device has a second configuration in which the arcuate segments extend out from the band and the displays are coplanar. FIG. 20 shows this device in its first configuration. FIG. 21 shows this device in its second configuration.

With respect to specific components, FIGS. 20 and 21 show (proximal-to-distal or elbow-to-finger) side views at two different times of a wearable computing device for the wrist and/or arm comprising: an inner band (or strap) 2001 which worn is around a person's wrist and/or arm; a primary display 2002 on the dorsal side of the device; a first secondary display 2003 on a first side (e.g. to the right of) of the primary display; a first movable arcuate segment 2005 which connects an edge of the first secondary display to the inner band; a second secondary display 2004 on a second side (e.g. to the left of) of the primary display; and a second movable arcuate segment 2006 which connects an edge of the second secondary display to the inner band; wherein the device has a first configuration wherein the first movable arcuate segment and second movable arcuate segment are folded in toward the inner band and wherein the primary display, first secondary display, and second secondary display are not coplanar; and wherein the device has a second configuration wherein the first movable arcuate segment and second movable arcuate segment extend out from the inner band and wherein the primary display, first secondary display, and second secondary display are coplanar. FIGS. 20 and 21 also include an outer band 2007 which is connected to the secondary displays.

In an example, a primary display can be attached to an inner band (or strap). In an example, a primary display can be attached to a housing which is attached to an inner band (or strap). In an example, a first side (or edge) of a secondary display can be attached to a primary display (or a housing to which the primary display is attached) and a second side (or edge) of the secondary display can be attached to a movable arcuate segment. In an example, secondary displays can be moveably connected to a primary display (or a housing to which the primary display is attached) by joints, hinges, axles, or folds. In an example, secondary displays can be moveably connected to moveable arcuate segments by joints, hinges, axles, or folds. In an example, the concavities of arcuate segments can open in the same directions as the concavities of proximal portions of the inner band in the first configuration, but can open in a different directions from those concavities in the second configuration.

In an example, the displays can all be flat. In an example, a flat primary display and a flat secondary display can be in virtual planes which intersect at 45 degree angle in the first configuration. In an example, a flat primary display and a flat secondary display can be in virtual planes which intersect at an angle between 30 and 60 degrees in the first configuration. In an example, one end of an arcuate segment can slide along a track on an inner band as the device transitions from its first configuration to its second configuration. In an example, one end of an arcuate segment can slide (away from the primary display) along a track on an inner band as the device transitions from its first configuration to its second configuration. In an example, one end of an arcuate segment can slide (toward the primary display) along a track on an inner band as the device transitions from its second configuration to its first configuration. In an example, an arcuate segment can be substantially aligned with (e.g. concentric or nested with) an inner band in the first configuration and can extend out from the inner band in the second configuration.

In an example, the device can be moved from its first configuration to its second configuration by pivoting or rotating secondary displays upward into the same virtual plane as the virtual plane of the primary display. In an example, the secondary displays can be locked, latched, or snapped into place in their second configuration, but can also be subsequently unlocked, unlatched, and/or unsnapped back into their first configuration. In an example, there can be one primary display and two secondary displays, one secondary display on either side of the primary display. In an example, there can be one primary display and four secondary displays, two secondary displays on either side of the primary display. In an example, the primary display and secondary displays can collectively span between 30% and 55% of the circumference of the person's wrist and/or arm when the device is in the first configuration. In an example, the primary display and secondary displays can collectively span between 50% and 80% of the person's wrist and/or arm when the device is in the first configuration. Other example variations discussed in this disclosure or in priority-linked disclosures can also be applied to this example where relevant.

Figure 22:
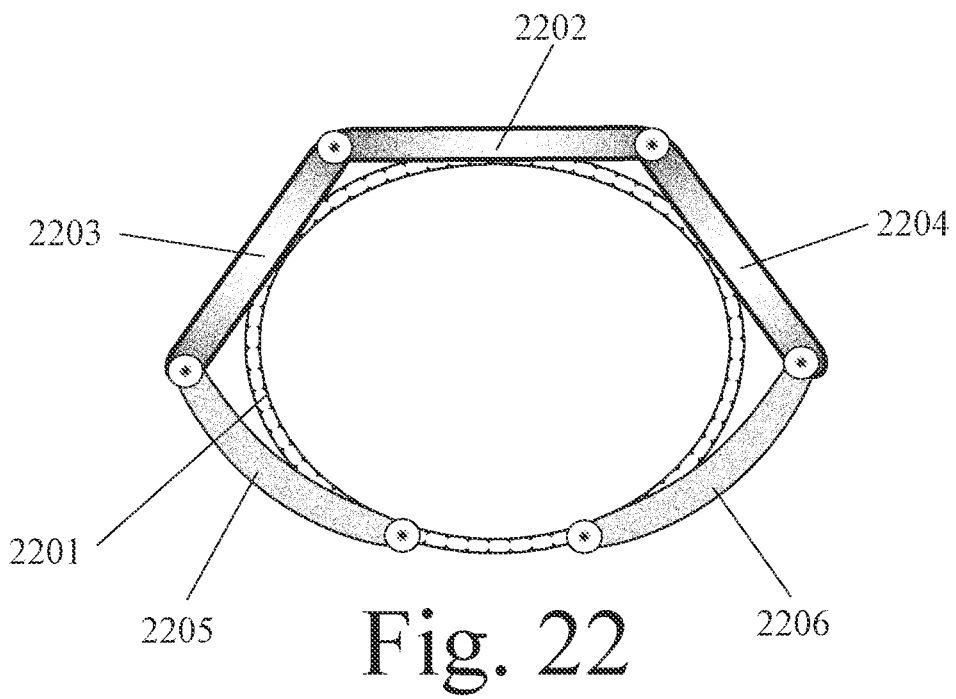
FIGS. 22 and 23 show a second example of a wrist-worn device with an inner band, a primary display, and secondary displays which are attached to folding arcuate segments.
Figure 23:
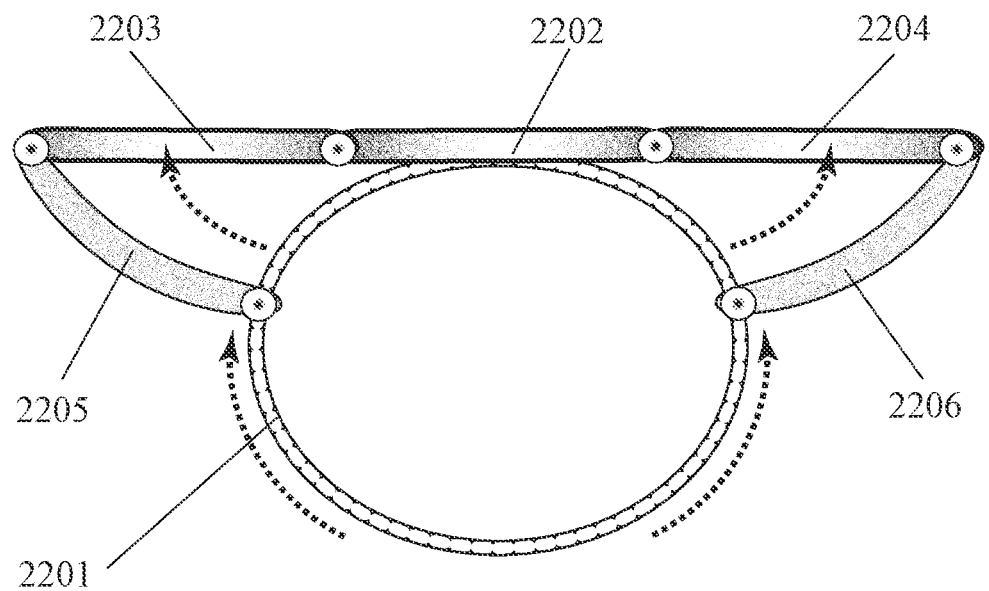

FIGS. 22 and 23 show side views at two different times of a wearable computing device for the wrist and/or arm comprising: a band worn around a person's wrist and/or arm; a primary display on the dorsal side of the band; a first secondary display on one side of the primary display; a first arcuate segment which connects the first secondary display to the band; a second secondary display on the other side of the primary display; and a second arcuate segment which connects the second secondary display to the band; wherein the device has a first configuration in which the arcuate segments are folded in toward the band and the displays are not coplanar; and wherein the device has a second configuration in which the arcuate segments extend out from the band and the displays are coplanar. FIG. 22 shows this device in its first configuration. FIG. 23 shows this device in its second configuration.

With respect to specific components, FIGS. 22 and 23 show (proximal-to-distal or elbow-to-finger) side views at two different times of a wearable computing device for the wrist and/or arm comprising: an inner band (or strap) 2201 which worn is around a person's wrist and/or arm; a primary display 2202 on the dorsal side of the device; a first secondary display 2203 on a first side (e.g. to the right of) of the primary display; a first movable arcuate segment 2205 which connects an edge of the first secondary display to the inner band; a second secondary display 2204 on a second side (e.g. to the left of) of the primary display; and a second movable arcuate segment 2206 which connects an edge of the second secondary display to the inner band; wherein the device has a first configuration wherein the first movable arcuate segment and second movable arcuate segment are folded in toward the inner band and wherein the primary display, first secondary display, and second secondary display are not coplanar; and wherein the device has a second configuration wherein the first movable arcuate segment and second movable arcuate segment extend out from the inner band and wherein the primary display, first secondary display, and second secondary display are coplanar.

The wearable computing device for the wrist and/or arm shown in FIGS. 22 and 23 can also be described as comprising: an inner band which configured to be worn around a person's wrist and/or arm; a primary display on a dorsal side of the device; a first secondary display on a first lateral side of the primary display; a first movable arcuate segment which connects an edge of the first secondary display to the inner band; a second secondary display on a second lateral side of the primary display; and a second movable arcuate segment which connects an edge of the second secondary display to the inner band; wherein the device has a first configuration in which the first movable arcuate segment and second movable arcuate segment are folded in toward the inner band and in which the primary display, the first secondary display, and the second secondary display are not coplanar; and wherein the device has a second configuration in which the first movable arcuate segment and the second movable arcuate segment extend out from the inner band and in which the primary display, the first secondary display, and the second secondary display are coplanar.

In an example, a primary display can be attached to an inner band (or strap). In an example, a primary display can be attached to a housing which is attached to an inner band (or strap). In an example, a first side (or edge) of a secondary display can be attached to a primary display (or a housing to which the primary display is attached) and a second side (or edge) of the secondary display can be attached to a movable arcuate segment. In an example, secondary displays can be moveably connected to a primary display (or a housing to which the primary display is attached) by joints, hinges, axles, or folds. In an example, secondary displays can be moveably connected to moveable arcuate segments by joints, hinges, axles, or folds. In an example, the concavities of arcuate segments can open in the same directions as the concavities of proximal portions of the inner band in the first configuration, but can open in a different directions from those concavities in the second configuration.

In an example, the displays can all be flat. In an example, a flat primary display and a flat secondary display can be in virtual planes which intersect at 45 degree angle in the first configuration. In an example, a flat primary display and a flat secondary display can be in virtual planes which intersect at an angle between 30 and 60 degrees in the first configuration. In an example, one end of an arcuate segment can slide along a track on an inner band as the device transitions from its first configuration to its second configuration. In an example, one end of an arcuate segment can slide (toward the primary display) along a track on an inner band as the device transitions from its first configuration to its second configuration. In an example, one end of an arcuate segment can slide (away from the primary display) along a track on an inner band as the device transitions from its second configuration to its first configuration. In an example, an arcuate segment can be substantially aligned with (e.g. concentric or nested with) an inner band in the first configuration and can extend out from the inner band in the second configuration.

In an example, the device can be moved from its first configuration to its second configuration by pivoting or rotating secondary displays upward into the same virtual plane as the virtual plane of the primary display. In an example, the secondary displays can be locked, latched, or snapped into place in their second configuration, but can also be subsequently unlocked, unlatched, and/or unsnapped back into their first configuration. In an example, there can be one primary display and two secondary displays, one secondary display on either side of the primary display. In an example, there can be one primary display and four secondary displays, two secondary displays on either side of the primary display. In an example, the primary display and secondary displays can collectively span between 30% and 55% of the circumference of the person's wrist and/or arm when the device is in the first configuration. In an example, the primary display and secondary displays can collectively span between 50% and 80% of the person's wrist and/or arm when the device is in the first configuration. Other example variations discussed in this disclosure or in priority-linked disclosures can also be applied to this example where relevant.

Figure 24:
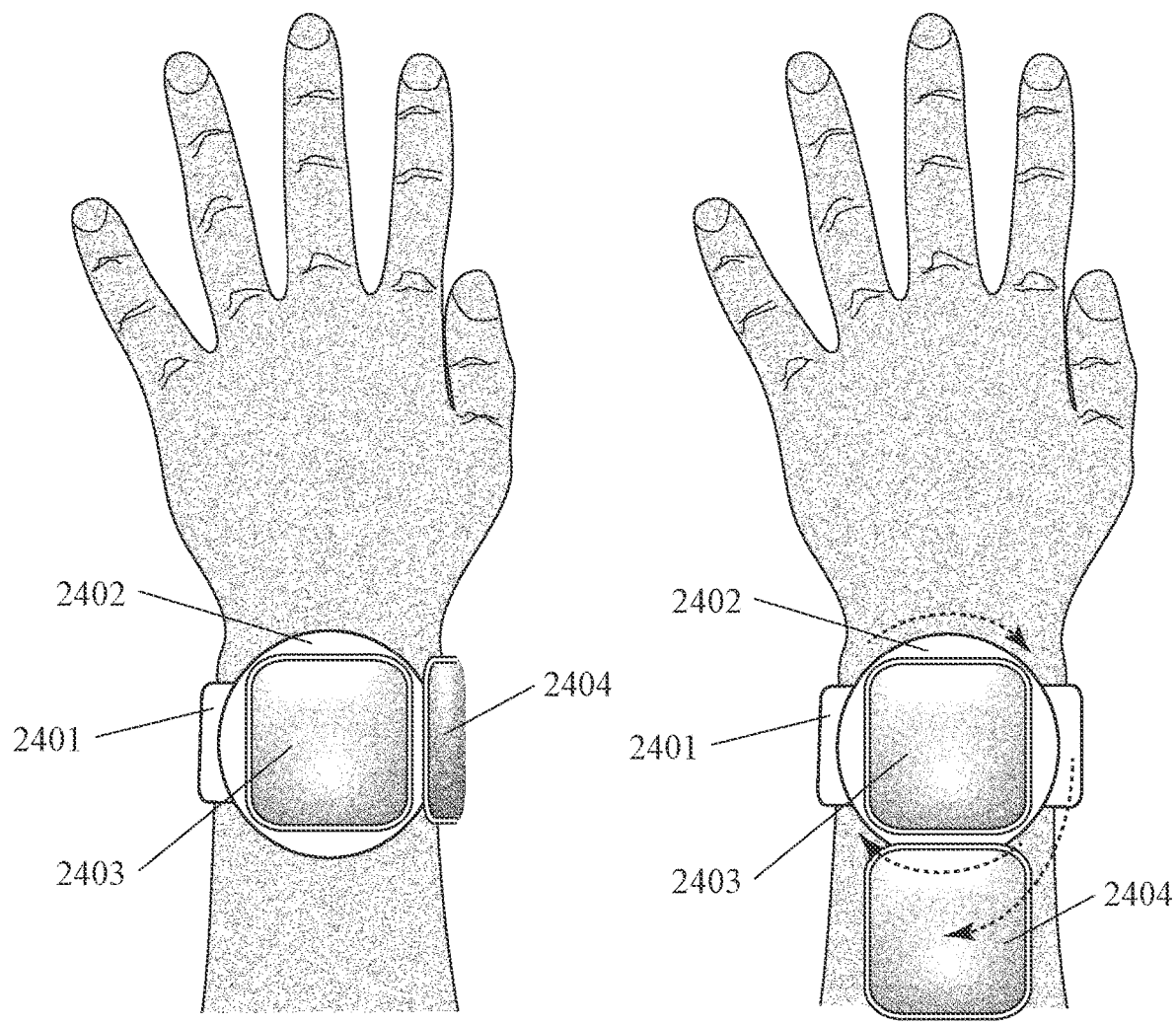
FIG. 24 shows a wrist-worn device with a primary display, a rotatable ring, and a secondary display attached to the ring.

FIG. 24 shows two views, at two different times, of a wearable computing device for the wrist and/or arm comprising: a band (or strap) 2401 worn around a person's wrist and/or arm; a primary display 2404 on a dorsal side of the band (or strap); a ring (or arcuate track) 2402 around the primary display; and a secondary display 2404 attached to the ring (or arcuate track); wherein the device has a first configuration in which the secondary display is on a lateral (e.g. right or left) side of the band; wherein the device has a second configuration in which the secondary display in on the dorsal side of the band; and wherein the device is changed from the first configuration to the second configuration by moving the secondary display around the ring (or arcuate track) or by rotating the ring (or arcuate track). The left portion of FIG. 24 shows this device in its first configuration and the right portion of FIG. 24 shows this device in its second configuration.

The example shown in FIG. 24 can also be described as a wearable computing device for the wrist and/or arm comprising: a band (or strap) worn around a person's wrist and/or arm; a primary display on a dorsal side of the band (or strap); a ring (or arcuate track) around the primary display; and a secondary display attached to the ring (or arcuate track); wherein the device has a first configuration in which the secondary display is to the right or left of the primary display; wherein the device has a second configuration in which the secondary display is proximal (e.g. closer to the person's elbow) relative to the primary display; and wherein the device is changed from the first configuration to the second configuration by moving the secondary display around the ring (or arcuate track) or by rotating the ring (or arcuate track).

The example shown in FIG. 24 can also be described as a wearable computing device for the wrist and/or arm comprising: a band (or strap) worn around a person's wrist and/or arm; a primary display on a dorsal side of the band (or strap); a ring (or arcuate track) around the primary display; and a secondary display attached to the ring (or arcuate track); wherein the device has a first configuration in which the secondary display is to the right or left of the primary display and is not coplanar with the primary display; wherein the device has a second configuration in which the secondary display is proximal (e.g. closer to the person's elbow) relative to the primary display and is coplanar with the primary display; and wherein the device is changed from the first configuration to the second configuration by moving the secondary display around the ring (or arcuate track) or by rotating the ring (or arcuate track).

The wearable computing device for the wrist and/or arm shown in FIG. 24 can also be described as comprising: a band which is configured to be worn around a person's wrist and/or arm; a primary display on a dorsal side of the band; a ring around the primary display; and a secondary display attached to the ring; wherein the device has a first configuration in which the secondary display is on a lateral side of the band; wherein the device has a second configuration in which the secondary display is on a dorsal side of the band; and wherein the device is changed from the first configuration to the second configuration by moving the secondary display around the ring and/or by rotating the ring.

In an example, a wearable computing device for the wrist and/or arm can comprise: a band (or strap) worn around a person's wrist and/or arm; a primary display on a dorsal side of the band (or strap); and a secondary display which is flexibly attached to the band and/or the primary display; wherein the device has a first configuration in which the secondary display is on a lateral (e.g. right or left) side of the band; wherein the device has a second configuration in which the secondary display in on the dorsal side of the band; and wherein the device is changed from the first configuration to the second configuration by rotating and/or pivoting the secondary display around the primary display.

In an example, a wearable computing device for the wrist and/or arm can comprise: a band (or strap) worn around a person's wrist and/or arm; a primary display on a dorsal side of the band (or strap); and a secondary display which is flexibly attached to the band and/or the primary display; wherein the device has a first configuration in which the secondary display is to the right or left of the primary display; wherein the device has a second configuration in which the secondary display is proximal (e.g. closer to the person's elbow) relative to the primary display; and wherein the device is changed from the first configuration to the second configuration by rotating and/or pivoting the secondary display around the primary display.

In an example, a wearable computing device for the wrist and/or arm can comprise: a band (or strap) worn around a person's wrist and/or arm; a primary display on a dorsal side of the band (or strap); and a secondary display which is flexibly attached to the band and/or the primary display; wherein the device has a first configuration in which the secondary display is to the right or left of the primary display and is not coplanar with the primary display; wherein the device has a second configuration in which the secondary display is proximal (e.g. closer to the person's elbow) relative to the primary display and is coplanar with the primary display; and wherein the device is changed from the first configuration to the second configuration by rotating and/or pivoting the secondary display around the primary display.

In an example, the primary display can have a rounded quadrilateral (e.g. quadrilateral with rounded vertexes) shape. In an example, the primary display can have a circular shape. In an example, the secondary display can have a rounded quadrilateral (e.g. quadrilateral with rounded vertexes) shape. In an example, the secondary display can have a circular shape. In an example, shapes of the primary display and the secondary display can be complementary. In an example, shapes of the primary display and the secondary display can fit together. In an example, the secondary display can have a concave side, the primary display can have a convex side, and the convex side can fit into the concave side. In an example, the secondary display can have a convex side, the primary display can have a concave side, and the convex side can fit into the concave side.

In an example, the secondary display can be locked, snapped, or latched onto a side of the band in the first configuration, but can subsequently be unlocked, unsnapped, or unlatched from this first configuration and moved to a location proximal (closer to the elbow) relative to the primary display in the second configuration. In an example, the secondary display can be locked, snapped, or latched into a location proximal (closer to the elbow) relative to the primary display in the second configuration, but can subsequently be unlocked, unsnapped, or unlatched from this second configuration and moved to the side of the band in the first configuration.

In an example, a secondary display can have protrusions (e.g. pins, teeth, or bearings) which fit into a track around a ring around the primary display, enabling the secondary display to be rotated around the primary display. In an example, a secondary display can have protrusions (e.g. pins, teeth, or bearings) which fit into a track around a housing for the primary display, enabling the secondary display to be rotated around the primary display. In an example, a housing to which a primary display is attached can have a rotatable ring around it, wherein the secondary display is attached to the rotatable ring, and wherein the device is changed from its first configuration to its second configuration (or vice versa) by rotating the ring. In another example, a side of a secondary display can be flexibly attached to a side of a primary display. In an example, the primary display is rotatable. In an example, rotation of the primary display causes the secondary display to move from a (first configuration) location to the right or left of the primary display to a (second configuration) location which is proximal (closer to the elbow) relative to the primary display. Other example variations discussed in this disclosure or in priority-linked disclosures can also be applied to this example where relevant.

Figure 25:
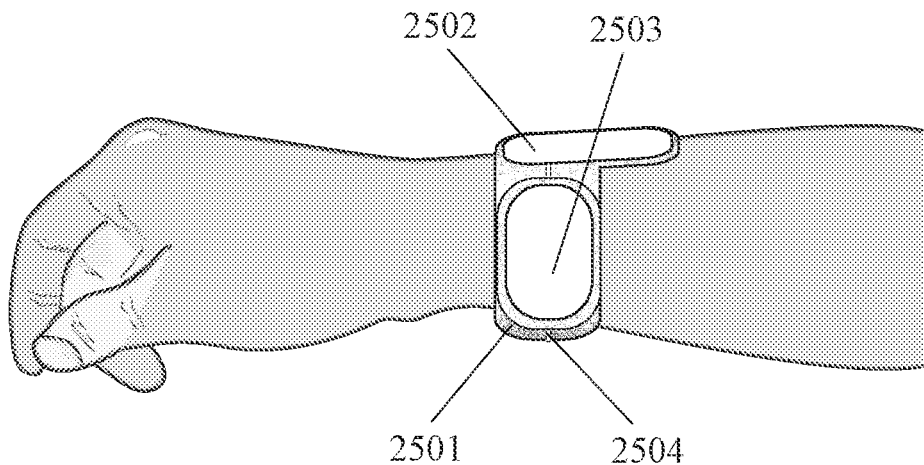
FIG. 25 shows a wrist-worn device with a primary display and a secondary display which can be pivoted and moved next to the primary display.
Figure 25:
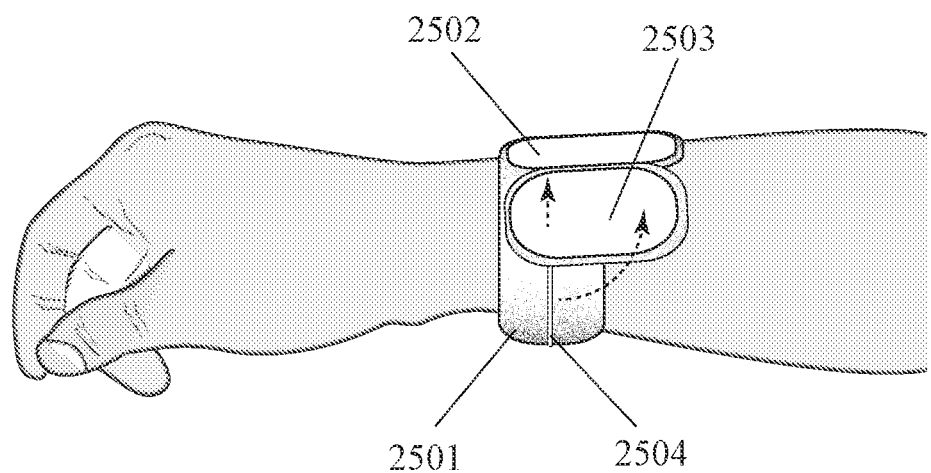

FIG. 25 shows two views, at two different times, of a wearable computing device for the wrist and/or arm comprising: a band (e.g. a band, strap, or bracelet) 2501 worn around a person's wrist and/or arm; a track (e.g. a track, guide, or ridge) 2504 around at least 20% of the circumference of the band; a primary display 2502 attached to a dorsal side of the band; and a movable longitudinal secondary display 2503 attached to the band; wherein the longitudinal secondary display has a first configuration in which its longitudinal axis is substantially parallel to the plane of the circumference of the band and it is a first maximum distance from the primary display; wherein the longitudinal secondary display has a second configuration in which its longitudinal axis is substantially perpendicular to the plane of the circumference of the band and it is a second maximum distance from the primary display; wherein the second maximum distance is less than the first distance; and wherein the secondary display is moved from its first configuration to its second configuration by being pivoted (e.g. pivoted or rotated) out from the band in a proximal (e.g. closer to the elbow) direction and also slid along the track toward the first display.

The upper portion of FIG. 25 shows this device when the secondary display is in the first configuration (e.g. on a lateral side of the band and oriented along the circumference of the band). The lower portion of FIG. 25 shows this device when the secondary display is in the second configuration (e.g. moved adjacent to, and aligned with, the primary display). In the second configuration, the primary and secondary displays combine to form a larger combined user interface display area. The secondary display can be in the first configuration wherein device is more compact and less restrictive of wrist and/or arm movement when a larger combined display area is not needed. The secondary display can be moved into the second configuration when a larger combined display area is needed.

In an example, this device can be moved manually from the first configuration to the second configuration, or vice versa, by the person wearing the device. In an example, a secondary display can be locked (e.g. attached, snapped, latched, clipped) into place in its second configuration, but subsequently unlocked (e.g. detached, unsnapped, unlatched, unclipped) from its second configuration to be moved back to its first configuration. In an example, a secondary display can be locked (e.g. attached, snapped, latched, clipped) to the primary display (or a housing of the primary display) in its second configuration, but subsequently unlocked (e.g. detached, unsnapped, unlatched, unclipped) from the primary display to be moved back to its first configuration.

In an example, a secondary display can be moved automatically from its first configuration to its second configuration, or vice versa, by an actuator in the device. In an example, automatic movement of a secondary display from its first configuration to its second configuration, or vice versa, can be triggered by one or more events selected from the group consisting of: body motion detected by a sensor in the device; an incoming communication; type of content displayed; a touch detected by a sensor in the device; and a voice command. In an example, the orientation and/or brightness of images on a secondary display can be automatically changed when the secondary display changes from its first configuration to its second configuration, or vice versa.

In an example, a primary display and/or a secondary display can have rectangular shapes. In an example, the vertexes of these rectangles can be rounded. In an example, a secondary display can span between 10% and 25 of the circumference of the band in its first configuration. In an example, a secondary display can be attached to (the track of) the band by a rotatable axle. In an example, a secondary display can pivot and/or rotate around this axle as it transitions from a first configuration to a second configuration. In an example, a primary display can be longitudinal, wherein its longitudinal axis is oriented in a proximal (e.g. closer to elbow) to distal (closer to a finger) direction. Alternatively, a primary display can have a shape which is circular or an equilateral polygon (e.g. a square, hexagon, or octagon).

In an example, first and/or secondary displays can be touch screens. In an example, first and secondary displays can show different images and/or serve different interface functions. In an example, one display can show an image of the wearer and the other display can show an image of a person with whom the wearer is communicating. In an example one display can show an image and the other display can show text or a control pad. In an example, the one display can display a summary of the information which is displayed in more detail on other displays. In another example, the two displays can show two portions of the same image. In an example, the two displays can combine to form a single larger display in the second configuration.

In an example, a device can further comprise a third display which is located on the opposite side of the person's wrist from the secondary display. Such a third display can have first and second configurations which are symmetric to those of the secondary display. The primary, secondary, and third displays can combine to form a large display. In an example, a combined large display can span between 20% and 50% of the circumference of the band. Other example variations discussed in this disclosure or in priority-linked disclosures can also be applied to this example where relevant.

Figure 26:
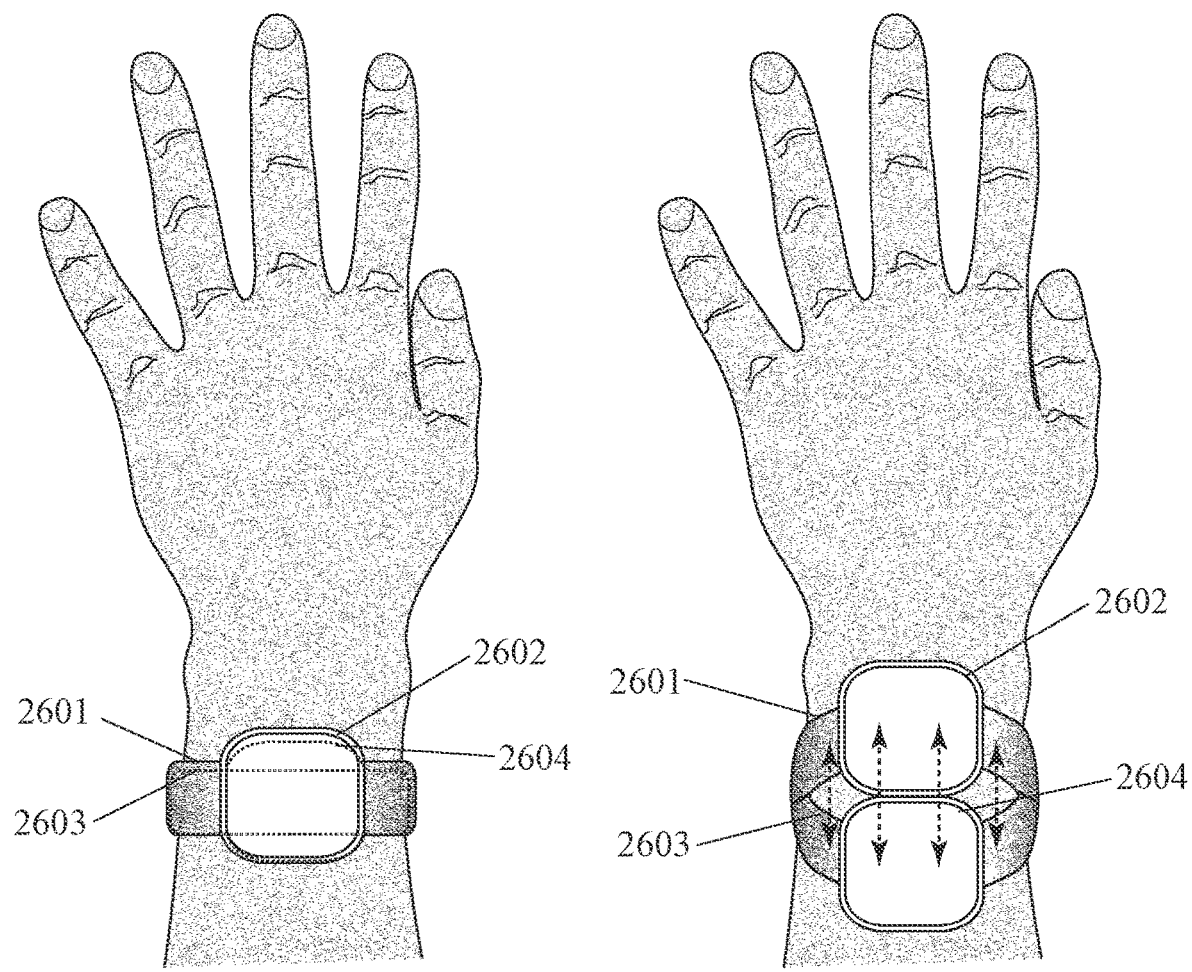
FIG. 26 shows a wrist-worn device with two displays on two branches of a bifurcated band, respectively, wherein the displays overlap in a first configuration and do not overlap in a second configuration.

FIG. 26 shows two views, at two different times, of a wrist-worn device with two displays on two branches of a bifurcated band, respectively, wherein the displays overlap in a first configuration and do not overlap in a second configuration. The left portion of FIG. 26 shows this device in the first configuration. The right portion of FIG. 26 shows this device in the second configuration. When the person wearing the device does not need a larger display, then the device can be kept in the relatively-compact first configuration which is less likely to restrict wrist movement or get snagged on an external object. When the person needs a larger display, then the two displays, and the two branches of the bifurcated band to which they are attached, are moved apart from each other, forming the second configuration which provides a larger combined display area.

With respect to specific components, FIG. 26 shows a wrist-worn device comprising: a band which is configured to be worn around a person's wrist and/or arm, wherein the band is bifurcated into a first branch of the band 2601 and second branch of the band 2603 on the dorsal side of the person's wrist and/or arm; a first display 2602 on the first branch of the band; and a second display 2604 on the second branch of the band; wherein the device has a first configuration in which the first display and the second display overlap; wherein the device has a second configuration in which the first display and the second display do not overlap; and wherein the device is changed from the first configuration to the second configuration by moving (e.g. sliding, extending, or pulling) the first and second displays apart from each other.

In an example, a first display can be on top of a second display in the first configuration (or vice versa), but the two displays be coplanar in the second configuration. In an example, a first display can cover a second display (or vice versa) in the first configuration, but both displays can be uncovered in the second configuration. In an example, a second display can be hidden underneath a first display in the first configuration (or vice versa), but both displays can be visible in the second configuration. In an example, a second display can be inside a housing to which a first display is attached in the first configuration, but can slide out from the housing in the second configuration. In an example, the two displays can slide apart from each other in proximal-to-distal (and/or distal-to-proximal) directions in order to change from the first configuration to the second configuration. In this example, proximal means closer to an elbow on the arm to which the device is attached and distal means closer to a finger on the arm to which the device is attached.

In an example, a first branch of the band can be on top of a second branch of the band in the first configuration (or vice versa), but the two branches of the band be coplanar in the second configuration. In an example, a first branch of the band can cover a second branch of the band (or vice versa) in the first configuration, but both branches of the band can be uncovered in the second configuration. In an example, a second branch of the band can be hidden underneath a first branch of the band in the first configuration (or vice versa), but both branches of the band can be visible in the second configuration. In an example, the two branches of the band can slide apart from each other in proximal-to-distal (and/or distal-to-proximal) directions in order to change from the first configuration to the second configuration.

In an example, there can be a gap between the two branches on the dorsal side of the band in the second configuration. This gap allows more airflow to the person's wrist and/or arm in the second configuration to reduce accumulation of moisture and/or discomfort. In an example, there can be an elliptical or oval shaped gap between the two branches on the dorsal side of the band in the second configuration. In an example, there can be a polygon-shaped gap between the two branches on the dorsal side of the band in the second configuration. In an example, there can be a convex gap between the two branches on the dorsal side of the band in the second configuration. In an example, there can be a fish-shaped convex gap between the two branches on the dorsal side of the band in the second configuration.

In an example, this device can be moved manually from the first configuration to the second configuration, or vice versa, by the person wearing the device. In an example, the two displays can be locked (e.g. attached, snapped, latched, clipped) into place in the second configuration, but subsequently unlocked (e.g. detached, unsnapped, unlatched, unclipped) from the second configuration to be moved back to the first configuration. In an example, the displays can be moved automatically from the first configuration to the second configuration, or vice versa, by an actuator in the device.

In an example, first and second displays can have rectangular shapes. In an example, the vertexes of these rectangles can be rounded. In an example, first and second displays can have circular shapes. In an example, first and second displays can be touch screens. In an example, first and second displays can show different images and/or serve different interface functions. In an example, one display can show an image of the wearer and the other display can show an image of a person with whom the wearer is communicating. In an example one display can show an image and the other display can show text or a control pad. In an example, the one display can display a summary of the information which is displayed in more detail on other displays. In another example, the two displays can show two portions of the same image. In an example, two displays can combine to form a single larger display in the second configuration. Other example variations discussed in this disclosure or in priority-linked disclosures can also be applied to this example where relevant.

I claim:

1. A wearable computing device for the wrist and/or arm comprising:
    an inner band which configured to be worn around a person's wrist and/or arm;
    a primary display on a dorsal side of the device;
    a first secondary display on a first lateral side of the primary display;
    a first movable arcuate segment which connects an edge of the first secondary display to the inner band;
    a second secondary display on a second lateral side of the primary display; and
    a second movable arcuate segment which connects an edge of the second secondary display to the inner band;
    wherein the device has a first configuration in which the first movable arcuate segment and second movable arcuate segment are folded in toward the inner band and in which the primary display, the first secondary display, and the second secondary display are not coplanar; and wherein the device has a second configuration in which the first movable arcuate segment and the second movable arcuate segment extend out from the inner band and in which the primary display, the first secondary display, and the second secondary display are coplanar.

\* \* \* \* \*